US012784891B2

(12) United States Patent
Eshel et al.

(10) Patent No.: US 12,784,891 B2
(45) Date of Patent: Nov. 3, 2026

(54) SYSTEM AND A METHOD FOR HEALTH AND DIET MANAGEMENT AND NUTRITIONAL MONITORING

(71) Applicant: MAKESENSE DIGITAL HEALTH TECHNOLOGIES LTD., Rishon-LeZion (IL)

(72) Inventors: Lior Eshel, Rishon-LeZion (IL); Alexander Tolmach, Haifa (IL)

(73) Assignee: MAKESENSE DIGITAL HEALTH TECHNOLOGIES LTD., Rishon-LeZion (IL)

( * ) Notice: Subject to any disclaimer, the term of this patent is extended or adjusted under 35 U.S.C. 154(b) by 928 days.

(21) Appl. No.: 17/610,912

(22) PCT Filed: May 12, 2020

(86) PCT No.: PCT/IL2020/050512

§ 371 (c)(1),
(2) Date: Nov. 12, 2021

(87) PCT Pub. No.: WO2020/230123

PCT Pub. Date: Nov. 19, 2020

(65) Prior Publication Data

US 2022/0215930 A1 Jul. 7, 2022

Related U.S. Application Data

(60) Provisional application No. 62/846,685, filed on May 12, 2019.

(51) Int. Cl.
*G16H 20/60* (2018.01)
*A61B 5/145* (2006.01)
(Continued)

(52) U.S. Cl.
CPC ......... *G16H 20/60* (2018.01); *A61B 5/14532* (2013.01); *G16H 50/20* (2018.01); *G16H 50/30* (2018.01)

(58) Field of Classification Search
CPC ........ G16H 20/60; G16H 50/30; G16H 50/20; A61B 5/14532
(Continued)

(56) References Cited

U.S. PATENT DOCUMENTS 8,543,454 B2 9/2013 Fleischman
2006/0062859 A1 * 3/2006 Blum ..................... A61K 45/06 424/769

(Continued)

FOREIGN PATENT DOCUMENTS

EP 3387989 A1 10/2018
WO 2009016050 A1 2/2009

(Continued)

OTHER PUBLICATIONS

De Toro-Martín J, Arsenault BJ, Després JP, Vohl MC. Precision Nutrition: A Review of Personalized Nutritional Approaches for the Prevention and Management of Metabolic Syndrome. Nutrients. Aug. 22, 2017;9(8):913. (Year: 2017).*

(Continued)

*Primary Examiner* — Amber A Misiaszek
(74) *Attorney, Agent, or Firm* — GREENBERG TRAURIG, LLP

(57) ABSTRACT

A computerized system for utilizing a machine learning system for managing a subject's nutrition. The system includes a processor and memory circuitry (PMC) configured to provide data indicative of the level of a biomarker in a bodily fluid of the subject, then filtering the data indicative of the measured biomarker level of the subject, to produce data indicative of estimates of unknown variables utilizing a
(Continued)

stored set of personalized filter parameter values that characterize the subject, and inputting to a machine learning system and processing the data indicative of the estimates of unknown variable utilizing a stored set of personalized machine learning parameter values that characterize the subject, for determination of nutrition analysis that includes identification of real carbohydrate content consumed by the subject and possibly of real retroactive meal times.

20 Claims, 8 Drawing Sheets

(51) Int. Cl.
*G16H 50/20* (2018.01)
*G16H 50/30* (2018.01)

(58) Field of Classification Search
USPC .............................................................. 705/2
See application file for complete search history.

(56) References Cited

U.S. PATENT DOCUMENTS

| | | | | |
|---|---|---|---|---|
| 2009/0177068 | A1* | 7/2009 | Stivoric | A61B 5/0022 600/365 |
| 2011/0206610 | A1* | 8/2011 | Rothbard | A61P 5/38 424/9.1 |
| 2013/0158368 | A1* | 6/2013 | Pacione | A61B 5/0002 600/595 |
| 2014/0073892 | A1 | 3/2014 | Randloev et al. | |
| 2017/0131262 | A1* | 5/2017 | Horning | A23L 33/30 |
| 2017/0249445 | A1 | 8/2017 | Devries et al. | |
| 2017/0332951 | A1* | 11/2017 | Ahmad | G16H 50/20 |
| 2018/0368782 | A1 | 12/2018 | Mori et al. | |
| 2019/0035159 | A1 | 1/2019 | Tran et al. | |
| 2021/0104129 | A1 | 4/2021 | Srinivasan | |

FOREIGN PATENT DOCUMENTS

| | | | |
|---|---|---|---|
| WO | 2016/130535 | A2 | 8/2016 |
| WO | 2017/105600 | A1 | 6/2017 |

OTHER PUBLICATIONS

Salzsieder et al., Computer-aided systems in the management of type I diabetes: the application of a model-based strategy, Computer Methods and Programs in Biomedicine, 32:215-224 (1990).

Richard N. Bergman, "Toward Physiological Understanding of Glucose Tolerance", Diabetes 1989, 38 (12) 1512-1527.

Richard N. Bergman, Minimal Model: Perspective from 2005. Horm. Res. 2005;64 (suppl. 3):8-15.

Burke et al., "Self-Monitoring in Weight Loss: A Systematic Review of the Literature", J. Am. Diet Assoc. Jan. 2011; 111(1): 92-102.

Carbonnel et al., "Effect of the energy density of a solid-liquid meal on gastric emptying and satiety.", Am J. Clin. Nutr. Sep. 1994;60(3):307-11.

Dalla Man et al., "Meal Simulation Model of the Glucose-Insulin System", IEEE Trans Biomed Eng. Oct. 2007;54(10):1740-9.

Evert et al., "Nutrition Therapy for Adults With Diabetes or Prediabetes: A Consensus Report a Consensus Report", Diabetes Care vol. 42, May 2019.

Macdonald, "Physiological regulation of gastric emptying and glucose absorption", Diabet. Med. Sep. 1996;13(9 Suppl 5):S11-5. Review.

Maughan et al., "Methods for the assessment of gastric emptying in humans: an overview", Diabet. Med. Sep. 1996;13(9 Suppl 5):S6-10. Review.

Nucci et al., "Models of subcutaneous insulin kinetics. A critical review", Comput. Methods Programs Biomed 62(3):249-257 (2000).

Oviedo et al., "A review of personalized blood glucose prediction strategies for T1DM patients", Int. J. Numer. Method Biomed. Eng. Jun. 2017;33(6).

Pearson et al., "A Mathematical Model of the Human Metabolic System and Metabolic Flexibility", Bull Math Biol. Sep. 2014;76(9):2091-121.

Ramkisson et al., "Unannounced Meals in the Artificial Pancreas: Detection Using Continuous Glucose Monitoring", Sensors (Basel). Mar. 16, 2018;18(3).

Rozendaal et al., "Model-based analysis of postprandial glycemic response dynamics for different types of food", Clinical Nutrition Experimental, vol. 19, Jun. 2018, pp. 32-45.

Samadi et al., "Meal Detection and Carbohydrate Estimation Using Continuous Glucose Sensor Data", IEEE J Biomed Health Inform. May 2017;21(3):619-627.

Sushil Chordia, "Here's how Bing predicts possible outcomes of leading global sporting events", https://www.microsoft.com/en-in/msidc/blogs/Articles/Here-s-how-Bing-predicts-possible-outcomes-of-leading-global-sporting-events/75c29b07-a%E2%80%A6 (2018).

Ivan Contreras, "Personalized blood glucose prediction: A hybrid approach using grammatical evolution and physiological models" PLOS One | https://doi.org/10.1371/journal.pone.0187754 (2017).

Davies et al., "Management of Hyperglycemia in Type 2 Diabetes, 2018. A Consensus Report by the American Diabetes Association (ADA) and the European Association for the Study of Diabetes (EASD)", Diabetes Care Sep. 2018; dci180033.

* cited by examiner

FIG. 4A
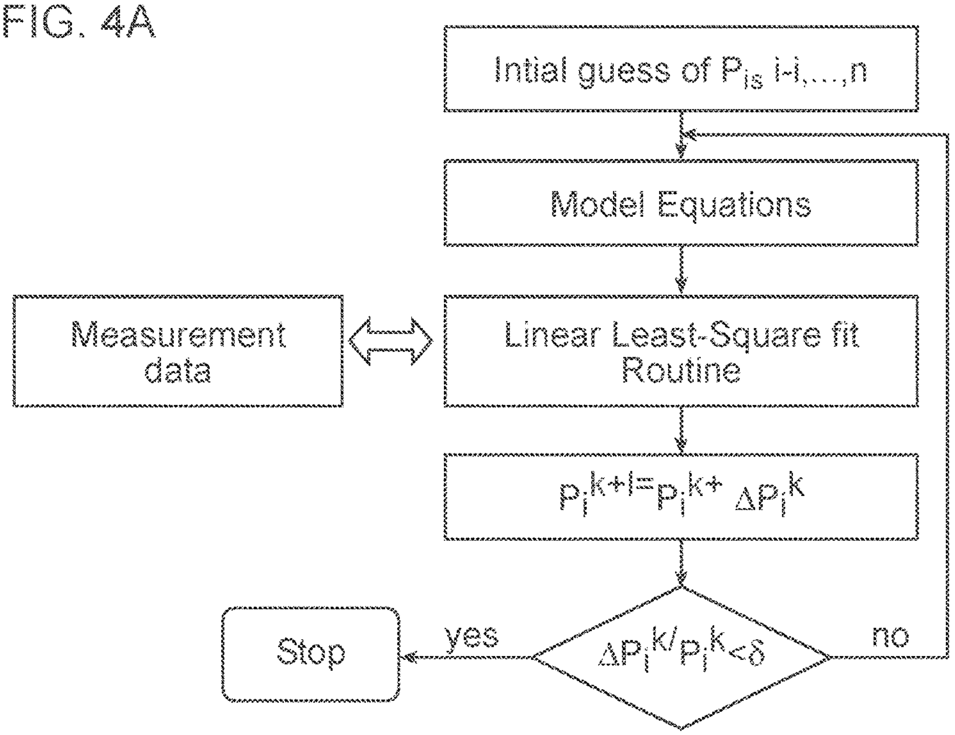
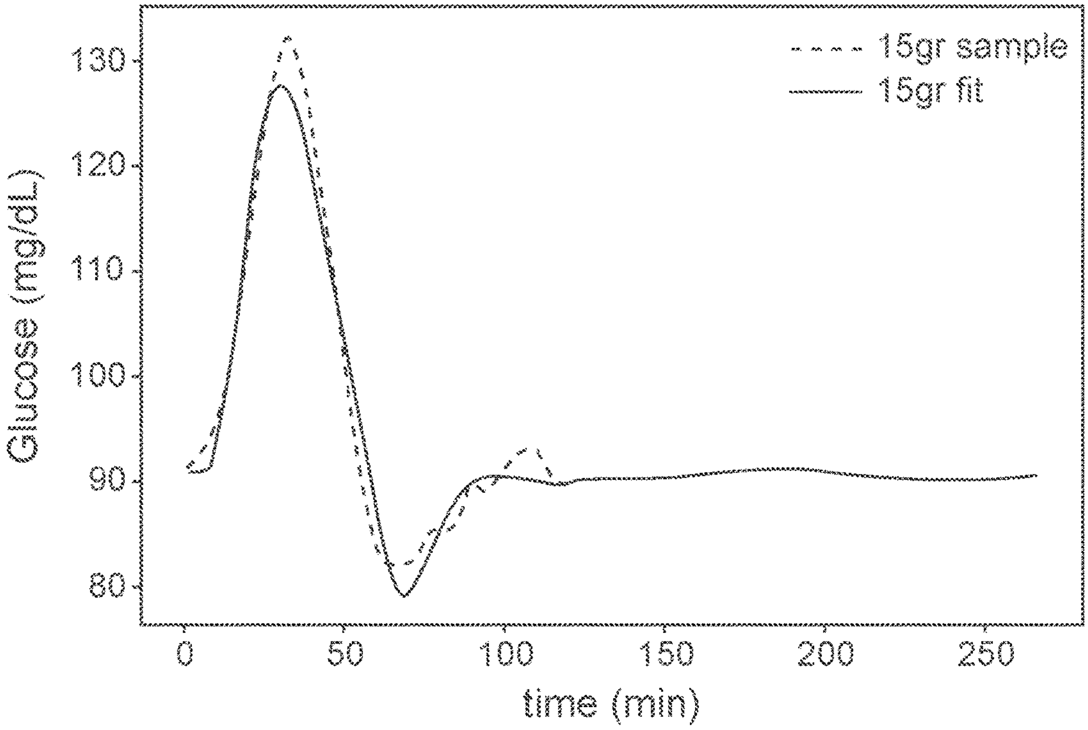
FIG. 4B

SYSTEM AND A METHOD FOR HEALTH AND DIET MANAGEMENT AND NUTRITIONAL MONITORING

CROSS-REFERENCE TO RELATED APPLICATIONS

This application claims benefit under 35 U.S.C. § 119(e) to U.S. Provisional Patent Application No. 62/846,685 entitled: A SYSTEM AND A METHOD FOR HEALTH AND DIET MANAGEMENT AND NUTRITIONAL MONITORING filed May 12, 2019 which is herein incorporated by reference in its entirety for all purposes and is annexed herewith and entitled “Annex”.

TECHNOLOGICAL FIELD

The present invention is in the field of health management, in particular in the field of nutrition management.

BACKGROUND ART

References considered to be relevant as background to the presently disclosed subject matter are listed below:

Bergman, *Diabetes* 1989, 38 (12) 1512-1527.
Bergman, Minimal Model: Perspective from 2005. *Horm. Res.* 2005; 64 (suppl. 3):8-15.
Burke et al., Self-Monitoring in Weight Loss: A Systematic Review of the Literature *J. Am. Diet Assoc.* 2011 January; 111(1): 92-102.
Carbonnel et al., Effect of the energy density of a solid-liquid meal on gastric emptying and satiety. Am J. Clin. Nutr. 1994 September; 60(3):307-11.
Contreras et al., Personalized blood glucose prediction: A hybrid approach using grammatical evolution and physiological models. PLoS One. 2017 Nov. 7; 12(11).
Dalla Man et al., Meal Simulation Model of the Glucose-Insulin System. *IEEE Trans Biomed Eng.* 2007 October; 54(10): 1740-9.
Davies et al., Management of Hyperglycemia in Type 2 Diabetes, 2018. A Consensus Report by the American Diabetes Association (ADA) and the European Association for the Study of Diabetes (EASD). *Diabetes Care* 2018 September; dci 180033.
Ingels et al., The Effect of Adherence to Dietary Tracking on Weight Loss: Using HLM to Model Weight Loss over Time. *Journal of Diabetes Research Volume* 2017 (12), 1-8.
Kanderian et al., Identification of Intraday Metabolic Profiles during Closed-Loop Glucose Control in Individuals with Type 1 Diabetes. *J Diabetes Sci Technol.* 2009 Sep. 1; 3(5):1047-57.
Macdonald, Physiological regulation of gastric emptying and glucose absorption. *Diabet. Med.* 1996 September; 13(9 Suppl 5):S11-5. Review.
Maughan and Leiper Methods for the assessment of gastric emptying in humans: an overview. *Diabet. Med.* 1996 September; 13(9 Suppl 5):S6-10. Review.
Nucci and Cobeli, Models of subcutaneous insulin kinetics. A critical review. *Comput. Methods Programs Biomed* 62(3): 249-257 (2000).
Oviedo et al., A review of personalized blood glucose prediction strategies for T1DM patients. *Int. J. Numer. Method Biomed. Eng.* 2017 June; 33(6).
Pearson et at, A Mathematical Model of the Human Metabolic System and Metabolic Flexibility. *Bull Math Biol.* 2014 September; 76(9):2091-121.

Ramkissoon et al., Unannounced Meals in the Artificial Pancreas: Detection Using Continuous Glucose Monitoring. Sensors (Basel). 2018 Mar. 16; 18(3).
Rozendaal et al., Model-based analysis of postprandial glycemic response dynamics for different types of food. Clinical Nutrition Experimental, Volume 19, June 2018, Pages 32-45.
Samadi et al., Meal Detection and Carbohydrate Estimation Using Continuous Glucose Sensor Data. *IEEE J Biomed Health Inform.* 2017 May; 21(3):619-627.
US 2018/0368782
EP 3387989
US 2017/0249445

Acknowledgement of the above references herein is not to be inferred as meaning that these are in any way relevant to the patentability of the presently disclosed subject matter.

BACKGROUND

Nutritional monitoring is desired in various scenarios, related to health and fitness, such as in a weight loss diet in which the subject is recommended to limit his/her consumption of some nutrients, such as carbs, to achieve weight loss goals, or on a weight gain diet in which the interest is in an increase of calorie consumption. In the medical field, for instance, patients with diabetes may be instructed to limit their consumption of carbs and calories as part of a nutritional therapy to improve the ability of the body to control blood glucose levels and to achieve remission of the diabetic condition.

Both in the case of a self-managed diet and in the case of a diet that is guided and accompanied by a professional, some of the most desired feedbacks are quantity and nutritional composition of consumed food during the day and times of foods consumption. The feedback would help the individual to control his/her nutrition on everyday routine. It would also help both the individual and the dietitian to retrospectively identify nutritional patterns and habits that hinder the achievement of dietary goals.

Studies have shown that receiving feedback while on diet, and specifically self-monitoring of consumed foods, helps achieving dietary goals. For instance, a publication of the ADA (American Diabetes Association) and the EASD (European Association for the study of Diabetes) (Davies et al.) states that the most effective nonsurgical strategies for weight reduction involve food substitution and intensive, sustained counseling with a physician, a dietitian or a nutritionist. Burke et al. is an article that includes a review of 22 studies performed between 1993-2009. The authors concluded that more frequent self-monitoring was consistently and significantly associated with weight loss compared to less frequent self-monitoring. Ingels et al describes a study in which 1,685 participants tracked their food intake for the duration of 12 months. The participants were divided to 3 groups: rare trackers (<33% total days tracked), inconsistent trackers (33-66% total days tracked), and consistent trackers (>66% total days tracked) and it was shown that only consistent trackers had significant weight loss (−9.99 pounds)

An existing widespread tool for nutritional monitoring is a food diary. Nowadays, food diaries are available as web-based and/or smartphone applications. The user of a food diary records the content of consumed meals, by manually logging in types and estimated quantities of the consumed foods. The application, using knowledge of nutritional facts of different food types, calculates the nutritional composition of each meal. However, food diary outputs are highly inaccurate. Reasons are: user's estimation of food content and quantity is subjective and its accuracy depends on the user's ability to assess quantities precisely, consistently and without a bias. One of the causes of the inaccuracy in intake self-reporting is the inaccuracy of nutritional facts on food labels, nutrient content of a composite of the product is allowed to be inaccurate by as much as 20% according to FDA regulation (21 CFR 101.9—Nutrition labeling of food (g)(5)). Moreover, manual logging of meals tends to become tedious after a while and hence adherence periods of users to keeping a food diary are limited. More advanced methods try to tackle those problems by enabling logging by entering pictures of meals or scanning codes on packed food products. However, these solutions although providing some improvement still require high involvement from the user and their accuracy is limited.

In the field of Diabetes management several metabolic, mathematical models were developed. The aim of these models is to predict future blood glucose levels, based on past and present blood glucose level and nutritional composition of a consumed meal. This prediction is desired since insulin that is provided either by an injection or by a permanent insulin pump, takes time to affect the body. Hence estimation of future levels of blood glucose is needed, in order provide alert and/or to regulate dosages of injected insulin in an artificial pancreas, and/or in a hybrid closed loop system.

Some models that link consumption of carbs to the response of blood glucose levels (that can be monitored using a CGM), are described in Kanderian et al, Bergman, 2005, and Dalla Man et al. Models that link consumption of mixed meals and blood glucose levels are described in Rozendaal et al and Pearson et al. Contreras et al and Oviedo et al used Machine Learning and other advanced techniques for the predication of blood glucose levels for diabetics.

Samadi et al. and Ramkissoon et al. attempted to perform carbohydrates estimation and/or unannounced meal detection for use in artificial pancreas based on CGM measurements.

US2018/0368782 describes a meal and mealtime detection system, that is based on arm motion and heart rate sensors.

EP3387989A1 describes a method for identifying when has subject has eaten food. The method is based on heart rate variability measurement and carbon dioxide in the environment of the subject.

US2017/0249445 describes a system comprising a biosensor configured to collect pulse profile data and a processing circuit that is configured to generate a nutritional intake value such as calorie intake.

General Description

In a first of its aspects, the present invention provides a method for managing a subject's nutrition, the method comprising:

a. measuring continuously the level of a biomarker in a bodily fluid of the subject;
b. generating a nutritional analysis using a learning personalized metabolic model and a training procedure, wherein said nutritional analysis comprises retroactively identifying consumed meal content and selectively identifying meal times; and
c. adjusting the subject's subsequent food consumption according to the identified consumed meal content and selectively identified meal times.

In one embodiment, the method further comprising providing the patient with nutritional management, wherein said nutritional management includes at least one of:

a. detecting at least one eating habit and/or pattern of the subject;
b. evaluating the subject's success in reaching a diet goal; and
c. providing dietary suggestions for glycemic and weight control.

In some embodiments, said measured biomarker is selected from a group that includes glucose, triglycerides and urea.

In some embodiments, said measured consumed meal content is selected from a group that includes carbohydrates, fat and protein.

In one embodiment, the subject's glucose level is measured using at least one biosensor.

In some embodiments, said biosensor is selected from a group that includes an invasive biosensor, a semi-invasive biosensor, a minimally invasive biosensor, a non-invasive biosensor and a combination thereof.

In one embodiment, said biosensor is attached to the subject's skin.

In some embodiments, said at least one biosensor is a patch or a subcutaneous Continuous Glucose Monitoring (CGM) sensor.

In some embodiments, said bodily fluid is selected from a group that includes blood, plasma, and interstitial fluid.

In some embodiments, said learning personalized metabolic model comprises identifying value ranges for a set of personalized metabolic parameters.

In some embodiments, said personalized metabolic parameter set comprises at least one of glucose effectiveness, insulin sensitivity, basal glucose, basal insulin, blood glucose rate of appearance, rate of pancreatic release after glucose bolus, rate of insulin clearance, the amount of non-monomeric insulin in the subcutaneous space, the amount of monomeric insulin in the subcutaneous space, gastric emptying rate, Stomach Rate of Appearance constant (Srat), Specific emptying rate, absorption constant, effective volume of the glucose compartment, and glucose rate of appearance in plasma.

In some embodiments, the identification of the personalized metabolic parameter value ranges comprises obtaining the subject's personal information and/or obtaining calibration meal data.

In some embodiments, said personal information comprises one or more of the subject's age, gender, race, ethnicity, weight, height, BMI (Body Mass Index), resting metabolic rate (RMR), basal metabolic rate (BMR), resting pulse, microbiome analysis, genetic information, medical condition, or medical history.

In some embodiments, said personal information is used to assign a general value range for each of said personalized metabolic parameters according to known values in a population.

In some embodiments, said calibration meal data is obtained by:

a. Providing the subject with one or more calibration meals;
b. Measuring continuously the level of a biomarker in a bodily fluid in response to the consumption of the one or more calibration meals; and
c. Performing model parameter estimation using a fitting technique.

In some embodiments, said model parameter estimation comprises fitting the measured biomarker level to the personalized metabolic parameter set that gives the best fit, thereby obtaining a specific value range for each of said personalized metabolic parameters.

In one embodiment, said specific value range is smaller than the general value range.

In some embodiments, the method further comprises measuring the subject's heart rate and/or temperature.

In some embodiments, the method further comprises using a weighed averaging technique to combine said personal information and said calibration meal data to arrive at the personalized metabolic parameter ranges.

In some embodiments, said learning personalized metabolic model comprises a digestion model and a blood regulation model.

In some embodiments, said learning personalized metabolic model comprises the following set of equations:

$$r_{GUT} = SER_0 \cdot \log(1 + C_H(t) \cdot S_{RAT})$$

wherein $r_{GUT}$—is the gastric emptying rate

Srat—Stomach Rate of Appearance constant.

$$\frac{dC}{dt} = -r_{GUT} + \delta_{Carbs}$$

$$\frac{dG_q}{dt} = -k_{abs} \cdot G_q + \frac{r_{GUT}}{V_G \cdot BW}$$

$$R_{G=} - k_{abs} \cdot G_q$$

Wherein

δCarbs—is the amount of carbs consumed during the time step $k_{abs}$—absorption constant $V_G$—is the effective volume of the glucose compartment (per kg of body weight)

BW—user bodyweight $R_G$—is the glucose rate of appearance in plasma.

In some embodiments, said training procedure is obtained by a. Generating multiple virtual data sets comprising:
   i. metabolic parameters that fall within the personalized metabolic parameter value ranges obtained using the learning personalized metabolic model;
   ii. data indicative of a plurality of meal scenarios and/or insulin injection scenarios;
b. Generating output virtual data set that includes data indicative of daily virtual levels of the biomarker based on the personalized metabolic parameters obtained using the learning personalized metabolic model;
c. Filtering the output virtual data set data obtained in (b) to produce estimates for unknown variables; and
d. Inputting to a Machine Learning (ML) system the estimates for unknown variables.

In some embodiments, said unknown variables are selected from the group that includes of carbohydrates intake during the last time step (dC), insulin injection during the last time step (dI), carbohydrates amount in stomach compartment, Carbohydrates amount in the gut compartment (Gq), plasma glucose concentration (G), active insulin (X), plasma insulin (I) and the amount of non-monomeric and monomeric insulin in subcutaneous compartments (Isc1/Isc2).

In one embodiment, said parameter sets that fall within said personalized metabolic parameter value ranges are random parameter sets.

In one embodiment, said plurality of meal scenarios and/or insulin injection scenarios is a plurality of random meal scenarios and/or insulin injection scenarios.

In some embodiments, said method further comprises: providing an estimation of at least one of glucose sensitivity, insulin resistance, continuous blood insulin level, risk of diabetes or risk of a heart disease.

In some embodiments, said measured biomarker is glucose.

In some embodiments, said subject is a diabetes patient.

In some embodiments, said method further comprises adjusting the patient's subsequent insulin administration according to the identified consumed meal content and selectively identified meal times.

In another aspect, the present invention provides a method for regulating the glucose level of a subject suffering from diabetes, the method comprising:

a. measuring continuously the level of glucose in a bodily fluid of the subject;
b. generating a nutritional analysis using a learning personalized metabolic model and a training procedure, wherein said nutritional analysis comprises retroactively identifying consumed carbohydrate content and selectively identifying meal times; and
c. adjusting the subject's subsequent insulin dosing regimen according to the identified meal times and carbohydrate content.

In another one of its aspects, the present invention provides a computerized method for training a machine learning system for managing a subject's nutrition, the method comprising, a processor and memory circuitry (PMC):

a. providing a learning personalized metabolic model that includes a plurality of identified personalized metabolic parameters that are associated with the subject, wherein each parameter having a respective range of values;
b. providing input virtual data sets that include data indicative of virtual metabolic parameter sets that fall within the personalized metabolic parameter value ranges and virtual meal scenarios each including virtual consumed carbohydrate content;
c. generating output virtual data sets that include data indicative of a set of virtual biomarker levels, using the learning personalized metabolic model and based on parameter sets that fall in said personalized metabolic parameter value ranges;
d. filtering the output virtual data sets to produce data indicative of estimates of unknown variables and determining and storing a set of personalized filter parameter values that were utilized in said filtering and which characterize the subject, and
e. inputting to a machine learning system a data training set, and processing the data for facilitating determination of nutrition analysis that includes identification of real retroactive carbohydrate content consumed by said given subject and selectively identified real retroactive meal times, based on measured subject's glucose level, and determining and storing a set of personalized machine learning parameter values that were utilized in said training and which characterize the subject.

In some embodiments, said data training set includes at least (i) the data indicative of virtual meal scenarios (ii) the data indicative of the estimates of unknown variables.

In some embodiments, said data training set further includes at least one of (i) the data indicative of said measured biomarker levels, and optionally (ii) data indicative of Insulin injection.

In some embodiments, said biomarker being glucose.

In some embodiments, the method further comprises receiving data indicative of heart rate and/or temperature.

In some embodiments, said unknown variables are selected from the group that includes carbohydrates intake during the last time step (dC), insulin injection during the last time step (dI), carbohydrates amount in stomach compartment, Carbohydrates amount in the gut compartment (Gq), plasma glucose concentration (G), active insulin (X), plasma insulin (I) and the amount of non-monomeric and monomeric insulin in subcutaneous compartments (Isc1/Isc2).

In some embodiments, said generation of virtual data sets comprises generation of parameter sets that fall within said personalized metabolic parameter value ranges and generation of data indicative of a plurality of meal scenarios and/or insulin injection scenarios.

In some embodiments, said parameter sets that fall within said personalized metabolic parameter value ranges are random parameter sets.

In some embodiments, said plurality of meal scenarios and/or insulin injection scenarios is a plurality of random meal scenarios and/or insulin injection scenarios.

In some embodiments, said method further comprises:

f. adjusting the subject's subsequent food consumption according to the identified consumed meal content and selectively identified meal times.

In some embodiments, the method further comprises providing the patient with nutritional management, wherein said nutritional management includes at least one of:

a. detecting at least one eating habit and/or pattern of the subject;
b. evaluating the subject's success in reaching a diet goal; and
c. providing dietary suggestions for glycemic and weight control.

In some embodiments, said method further comprises: providing an estimation of at least one of glucose sensitivity, insulin resistance, continuous blood insulin level, an/or risk of diabetes or risk of a heart disease.

In some embodiments, said subject is a diabetes patient.

In some embodiments, said method further comprises adjusting the patient's subsequent insulin administration according to the identified consumed carbohydrate content and selectively identified meal times.

In another one of its aspects, the present invention provides a computerized method for utilizing a machine learning system for managing a subject's nutrition, the method comprising, a processor and memory circuitry (PMC):

a. providing data indicative of the level of a biomarker in a bodily fluid of the subject;
b. filtering the data indicative of the measured biomarker level of the subject, to produce data indicative of estimates of unknown variables utilizing a stored set of personalized filter parameter values that characterize the subject; and
c. inputting to a machine learning system and processing the data indicative of the estimates of unknown variable utilizing a stored set of personalized machine learning parameter values that characterize the subject, for determination of nutrition analysis that includes identification of real carbohydrate content consumed by said subject and possibly of real retroactive meal times.

In some embodiments, the method further provides: inputting to the machine learning system at least one of: data indicative of measured biomarker level, data indicative of Insulin injection and data indicative of meal information.

In some embodiments, said biomarker levels being glucose levels.

In some embodiments, the method further comprises receiving data indicative of heart rate and/or temperature.

In some embodiments, said unknown variables are selected from the group that includes of carbohydrates intake during the last time step (dC), insulin injection during the last time step (dI), carbohydrates amount in stomach compartment, Carbohydrates amount in the gut compartment (Gq), plasma glucose concentration (G), active insulin action (X), plasma insulin (I) and the amount of non-monomeric and monomeric insulin in subcutaneous compartments (Isc1/Isc2).

In some embodiments, said method further comprises:

d. adjusting the subject's subsequent food consumption according to the identified consumed meal content and selectively identified meal times.

In some embodiments, the method further comprises providing the patient with nutritional management, wherein said nutritional management includes at least one of:

a. detecting at least one eating habit and/or pattern of the subject;
b. evaluating the subject's success in reaching a diet goal; and
c. providing dietary suggestions for glycemic and weight control.

In some embodiments, said method further comprises providing an estimation of at least one of glucose sensitivity, insulin resistance, continuous blood insulin level, risk of diabetes or risk of a heart disease.

In some embodiments, said subject is a diabetes patient.

In some embodiments, said method further comprises adjusting the patient's subsequent insulin administration according to the identified consumed carbohydrate content and selectively identified meal times.

In some embodiments, the model was trained using calibration meal data that included a first number of real calibration meals and a second number of virtual meals, wherein said second number is considerably larger than said first number.

In another one of its aspects, the present invention provides a computerized system for training a machine learning system for managing a subject's nutrition, the system comprising a processor and memory circuitry (PMC) configured to perform method steps of the computerized method of the invention, as described above.

In some embodiments, the system comprises a filtering system capable of processing the output virtual data sets to produce data indicative of the estimates of unknown variables and determining for storage the set of personalized filter parameter values that were utilized in said filtering and which characterize the subject.

In some embodiments, said filtering system is selected from the group that includes an Unscented Kalman filter (UKF) system, Extended Kalman Filter (EKF).

In some embodiments, the system comprises a Machine Learning (ML) system capable of processing the data indicative of a training set, to produce data facilitating determination of nutrition analysis that includes identification of real retroactive meal times and real carbohydrate content consumed by said given subject based on measured subject's biomarker level, and determining for storage a set of personalized machine learning parameter values that were utilized in said training and which characterize the subject.

In some embodiments, said ML system being of Convolutional Neural Networks (CNN) type.

In some embodiments, said ML system being of Recurrent Neural Network (RNN) type.

In some embodiments, said biomarker is glucose.

In another one of its aspects, the present invention provides a non-transitory computer readable medium comprising instructions that, when executed by a computer, cause the computer to perform method steps of the computerized method of the invention, as described above.

In another one of its aspects, the present invention provides a computerized system for utilizing a machine learning system for managing a subject's nutrition, the system comprising a processor and memory circuitry (PMC) configured to perform method steps of the computerized method, as described above.

In some embodiments, the system comprises a filtering system capable of processing the data indicative of the measured biomarker level of the subject, to produce data indicative of estimates of unknown variables utilizing the stored set of personalized filter parameter values that characterize the subject.

In some embodiments, said filtering system is selected from the group that includes an Unscented Kalman filter (UKF) system, and an Extended Kalman Filter (EKF).

In some embodiments, the system comprises a Machine Learning (ML) system capable of processing the data indicative of the estimates of unknown variable utilizing the stored set of personalized machine learning parameter values that characterize the subject, for determination of nutrition analysis that includes identification of real meal content consumed by said subject and possibly of real retroactive meal times.

In some embodiments, said ML system being of Convolutional Neural Networks (CNN) type.

In some embodiments, said ML system being of Recurrent Neural Network (RNN) type.

In some embodiments, said biomarker is glucose and said meal content is carbohydrate content.

In another one of its aspects, the present invention provides a non-transitory computer readable medium comprising instructions that, when executed by a computer, cause the computer to perform method steps of the computerized method of the invention, as described above.

BRIEF DESCRIPTION OF THE DRAWINGS

In order to better understand the subject matter that is disclosed herein and to exemplify how it may be carried out in practice, embodiments will now be described, by way of non-limiting example only, with reference to the accompanying drawings, in which:

FIG. 4A is a schematic representation of Levenberg-Marquardt least squares; algorithm;

FIG. 4B is a graph showing glucose level values (mg/dL) as a function of time (minutes) for a sample containing 15 grams glucose as compared with a 15 gram fit;

DETAILED DESCRIPTION OF EMBODIMENTS

Figure 1A:
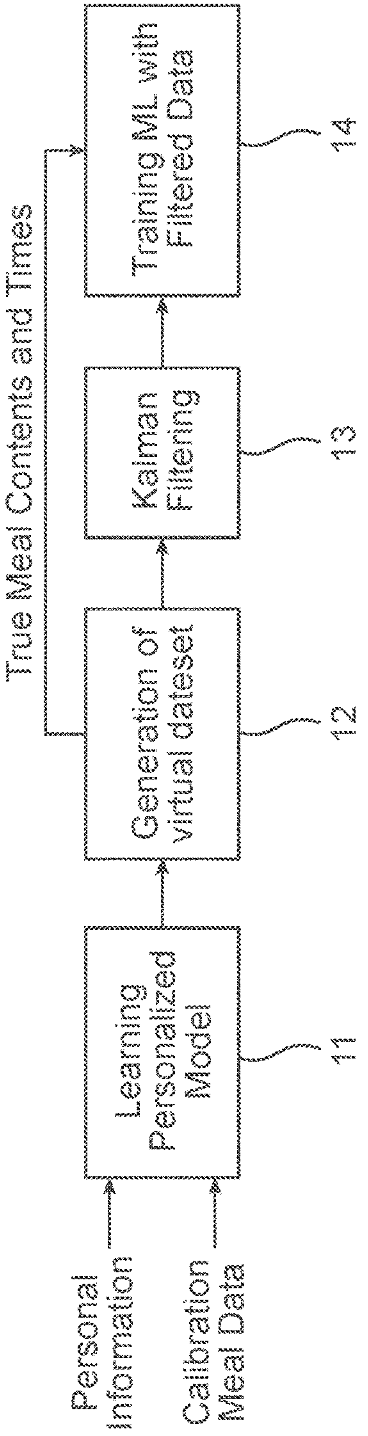
FIG. 1A illustrates schematically a sequence of operation of a learning personalized model and a training procedure for nutritional analysis and possibly nutritional management, in accordance with certain embodiments of the present invention.

The present invention relates to a method for health and diet/nutrition management comprising routine monitoring of the content of consumed meals (in particular the carbohydrate content) based on a unique learning metabolic model. As will be described below the method combines data obtained from continuously sampling biosensors and data analysis algorithms.

The method of the invention enables the evaluation of an overall nutritional regime based on analysis and identification of nutritional patterns and potential associated health risks (such as heart diseases, obesity, non-alcoholic fatty liver disease (NAFLD) and diabetes).

Some embodiments of the present invention, concern the provision of a feedback on the nutritional composition of a meal, for example calories, fat, proteins and in particular carbohydrates consumed in every meal and the time of meals as a tool to monitor, control and plan a diet. Therefore, in some embodiments of the present invention, a system and a method are provided for meal time detection and consumption measurement of carbohydrates, per meal, in a nonintrusive, and automated manner, using biosensors and a computerized system for training/using a machine learning system.

In some embodiments the method and system of the invention provide information on the individual's metabolic state as reflected by values of different metabolic model parameters (e.g. Glucose sensitivity or Insulin resistance) as will be explained in detail below.

Following the consumption of food, components/biomarkers in the blood stream are altered. The alteration in the levels of the blood components depends on the kind of food consumed. The pattern of alteration is highly correlated with the food's nutritional composition. For instance, the postprandial (after meal) change in glucose level in the blood is mostly correlated with carbohydrates (carbs) intake, although it may also be influenced by amounts of fats and protein in the meal consumed. Generally, the pattern of the change is characterized by an increase in glucose levels followed by a decrease with time.

The method of the invention comprises an initial training stage comprising a learning personalized model and a training procedure for learning the individual's personal metabolic parameters and physiological behavior, and a second stage in which this knowledge is implemented in an everyday manner together with continuous measurements of blood components/biomarkers (e.g. glucose) for monitoring the individual's nutrition including providing nutritional analysis, as will be described in detail below.

Therefore, in a first of its aspects, the present invention provides a method for managing a subject's nutrition, the method comprising:

a. measuring continuously the level of a biomarker in a bodily fluid of the subject;
b. generating a nutritional analysis using a learning personalized metabolic model and a training procedure, wherein said nutritional analysis comprises retroactively identifying meal times and consumed carbohydrate content; and
c. adjusting the subject's subsequent food consumption according to the identified meal times and selectively carbohydrate content.

The terms "subject", "individual" and "user" are used interchangeably herein to refer to a person, e.g. a person utilizing the method of the invention for managing his/her nutrition.

As used herein the term "nutrition" refers to the food consumed by an individual and is also referred to herein as a "diet".

As used herein the term "continuous measurement" or "measuring continuously" refers to a continuous monitoring of the level of a component present in a bodily fluid, preferably with minimal invasiveness. In particular, the present invention concerns the continuous monitoring of a biomarker, e.g. glucose in the blood or in the interstitial fluid.

In some embodiments, the continuous measurement is performed by periodic sampling of the bodily fluid. In some embodiments, the frequency of sampling is selected from a group which includes every 30 seconds, every 1 minute, every 5 minutes, every 10 minutes, every 15 minutes, at least 4 samples per hour, and at least 1 sample per hour.

In certain embodiments, the continuous measurement is performed using at least one biosensor.

The biosensor may be an invasive biosensor, a semi-invasive biosensor, a minimally invasive biosensor, a non-invasive biosensor or a combination thereof.

A non-limiting example of a biosensor that can be used in accordance with the present invention is the Semi-Invasive CGM (Continuous Glucose Monitoring) patch (produced for example by Abbott, Dexcom or Medtronic). This technology is based on sensing blood glucose level by a tiny filament inserted under to skin contacting interstitial fluid close to the capillary blood. The measurement signal is an electrical current that is proportional to the glucose concentration at the measurement site.

Non-limiting examples of non-invasive biosensors or sensing technologies include:

Optical Spectroscopy—for example Near Infrared Spectroscopy (for instance as described in Yadav et al., (2015) Biomedical Processing and Control, Vol. 18, 214-227). This method is based on the unique optical spectrum signature of each chemical component. This unique signature can be used to measure amounts of glucose or other components in the blood.

Electrical Bio-Impedance Spectroscopy—a method based on the changes in the blood cells membrane potential as a result of blood compound variations. Compound levels (e.g. glucose levels) can be estimated by determining the permittivity and conductivity of the membrane through the dielectric spectrum.

Also encompassed by the present invention are ultrasonic (acoustical) methods, chemical methods and thermal methods for continuously measuring glucose levels.

Different non-invasive measurement methods may be combined for improved accuracy, for example as described in Zhanxiao Geng et al (2017) Scientific Reports, Vol. 7 Article no. 12650 or Harman-Boehm et al (2010) J. Diabetes Sci. Technol. 1; 4(3): 583-95.

In some exemplary embodiments of the present invention, the sensor used for blood component response measurement is a CGM.

In some embodiments, the biosensors are in contact with the blood, or the interstitial fluid or the skin of the individual. The biosensor may be attached to the skin or be placed under the skin.

Some exemplary, non-limiting ways in which biosensors may be in contact with the body include: wearing the biosensor on the wrist or the arm (as a watch or a band or a bracelet), on the fingertip or on the knuckle (e.g. as a ring). Biosensors may be worn on the ear lobe (e.g. as an earring). Biosensors may by implanted subcutaneously. BioSensors may be integrated within a sticker patch, and worn on various body parts: for example on the arm, the belly, or the back.

In some embodiments, additional biosensors may be employed for measuring additional physiological parameters such as heart rate (e.g. using a fitness watch), heart rate variability (often considered indicative of stress-level), blood pressure, body temperature, humidity and movement (typically sensed by an accelerometer) and sleep time periods. One or more of these parameters may be incorporated into the learning metabolic model of the invention.

Additional physiological parameters may be measured using: an optical sensor showing the spectrum of reflected light from capillary blood or interstitial fluid; or a biosensor showing Dielectric Spectrum of some layers of the body including skin tissue, interstitial tissue and capillary blood; or a biosensor showing Electro-Chemical signal intensity, resulting from a chemical reaction between blood or interstitial fluid and some other material such as an enzyme. In all these examples the spectrum or the signal is indicative of blood composition.

As used herein the term "biomarker" refers to any blood component that is influenced by consumed food and that is measurable on a continued basis. Non-limiting examples of a biomarker are glucose, triglycerides and blood urea.

In a specific embodiment the measured biomarker in accordance with the invention is glucose.

Note that while for convenience the description is exemplified with reference to glucose, this is only an example. Other non-limiting examples being triglycerides, blood urea or others all as known per se.

As used herein the term "bodily fluid" is construed to include any human body fluid in which glucose levels may be measured. In particular the term encompasses, but is not limited to blood, plasma and interstitial fluid, e.g. subcutaneous interstitial fluid.

As indicated above, the method of the invention comprises generating a nutritional analysis using a learning personalized metabolic model and a computerized system for training a machine learning system.

As used herein the term "nutritional analysis" is construed to include retroactively identifying consumed content in a meal (e.g. carbohydrates) and possibly meal times.

As used herein the term "adjusting the subject's subsequent food consumption" is construed to include a change in the subject's next meals(s) content (e.g. the carbohydrate content), providing a recommendation for the next meal(s) content, providing information to a dietitian/physician/medical care giver for monitoring the subject's nutrition and/or health.

In a specific embodiment, if the nutritional analysis identifies that excess carbohydrates were consumed by the subject in a previous meal, the subject consumes (or is instructed to consume) a comparatively lower amount of carbohydrates in the next meal(s). In some embodiments, the term "excess carbohydrates" is defined in comparison to predefined diet requisitions prepared for the subject.

In a specific embodiment, if the nutritional analysis identifies that a low amount of carbohydrates was consumed by the subject in a previous meal, the subject consumes (or is instructed to consume) a comparatively higher amount of carbohydrates in the next meal(s). In some embodiments, the term "low amount of carbohydrates" is defined in comparison to predefined diet requisitions prepared for the subject.

In some embodiments, the method further comprising providing the patient with nutritional management.

As used herein the term "nutritional management" is construed to include at least one of:

a. detecting at least one eating habit and/or pattern of the subject;
b. evaluating the subject's success in reaching a diet goal; and
c. providing dietary suggestions for glycemic and weight control;

as will be discussed in more detail below, e.g. with respect to FIG. 9.

In certain embodiments, the nutritional management further comprises:

providing an estimation of at least one of glucose sensitivity, insulin resistance, continuous blood insulin level, risk of diabetes or risk of a heart disease.

The step of adjusting the subsequent food consumption can be performed by the subject and/or by a dietitian/physician/medical care giver.

In certain embodiments, the subject is a diabetes patient, e.g. a patient suffering from insulin dependent diabetes mellitus (IDDM).

Accordingly, in another embodiment, the present invention provides a method for regulating the glucose level of a subject suffering from diabetes, the method comprising:

a. measuring continuously the level of glucose in a bodily fluid of the subject;
b. generating a nutritional analysis using a learning personalized metabolic model and a training procedure, wherein said nutritional analysis comprises retroactively identifying consumed carbohydrate content and selectively identifying meal times; and
c. adjusting the subject's subsequent insulin dosing regimen according to the identified meal times and carbohydrate content.

According to such embodiments, the method provides diabetes management. As used herein the term "adjusting the subject's subsequent insulin dosing regimen" is construed to include adjusting insulin to carbohydrate content, adjusting insulin sensitivity factors, determining the time and dosing of subsequent insulin administration, feedback on self-estimation of carbohydrate content, for example in a hybrid closed loop system, such feedback is helpful in improving future assessments, support for medical care givers in assessing hypoglycemic/hyperglycemic events and directing treatment, affecting the calculation in an insulin calculator which determines insulin dosage in subsequent injections, alerting a caregiver concerning the IDDM patient's condition.

The terms "learning personalized metabolic model" and "learning personalized model" are used interchangeably herein and are construed to include a metabolic model in which, based on an information input (including, for example, personal information and calibration meal data as will be discussed below), value ranges for a set of personalized metabolic parameters of an individual are calculated.

In some embodiment, the set of personalized metabolic parameters of an individual comprises but is not limited to glucose effectiveness (designated $k_1$ or $S_G$), insulin sensitivity (designated for example $$S_I = \frac{k_3}{k_2}\Big),$$

basal glucose (Gb), basal insulin (Ib), blood glucose rate of appearance ($R_G$), Rate of pancreatic release after glucose bolus (gamma), rate of insulin clearance ($k_4$), the amount of non-monomeric insulin in the subcutaneous space (Isc1), the amount of monomeric insulin in the subcutaneous space (Isc2), gastric emptying rate ($r_{GUT}$), Stomach Rate of Appearance constant (Srat), absorption constant ($k_{abs}$), effective volume of the glucose compartment (per kg of body weight) ($V_G$), glucose rate of appearance in plasma ($R_G$).

In general, the method of the invention comprises two stages wherein the first stage is a training stage (as will be discussed with reference to FIG. 1A blow) comprising a learning personalized model and a training procedure including training a machine learning (ML) system (as will be discussed with reference also to FIG. 1B below) aimed at identifying and learning the user's general metabolic glucose response and performing nutritional analysis, and the second stage is the actual, everyday implementation of the method using a trained (ML) system which results in performing nutritional analysis of the subject based on real consumed meals, including retroactively identifying consumed carbohydrate content and possibly meals time. These data may then be used to manage the subject's nutrition.

During the training stage, the personalized metabolic parameters are identified, specific training data is generated, and an ML system is trained in order to detect meal times and carbohydrate contents.

In some embodiments, the information input for the learning personalized metabolic model comprises the subject's personal information and/or calibration meal data.

As used herein the term "personal information" is construed to include various variables including, but not limited to the user's age, gender, race, ethnicity, weight, height, BMI (Body Mass Index), resting metabolic rate (RMR), basal metabolic rate (BMR), resting pulse, microbiome analysis, genetic information, medical condition (e.g. known illnesses, medications taken), medical history (e.g. previous medical procedures and/or hospitalizations). The personal information can be provided by the user, e.g. via questionnaires, and/or medical records.

The personal information is used to assign a general value range for each of the personalized metabolic parameters according to known values in a population, as will be described below.

The terms "calibration meal data" and "reference meal data" are used interchangeably herein and are construed to include the information obtained by continuously monitoring the individual's glucose level during and after consumption of a calibration meal.

The terms "calibration meal" and "reference meal" are used interchangeably herein and are construed to include any portion of food with a known nutritional content, e.g. a known carbohydrate content. The calibration meal may be consumed once or a few times.

Accordingly, the individual may consume one, two, three, four, five, six or more calibration meals. The meals are consumed at the onset of the training stage. In some embodiments additional calibration meals are consumed or during the implementation stage, in order to recalibrate and adjust the learning system.

Continuously sampled biosensors data is recorded during and after consumption of the calibration meal with the known content, thereby generating data of the actual glucose response levels of the individual.

The Learning Personalized Model

As indicated above, the input data is introduced into a learning personalized model.

Figure 2:
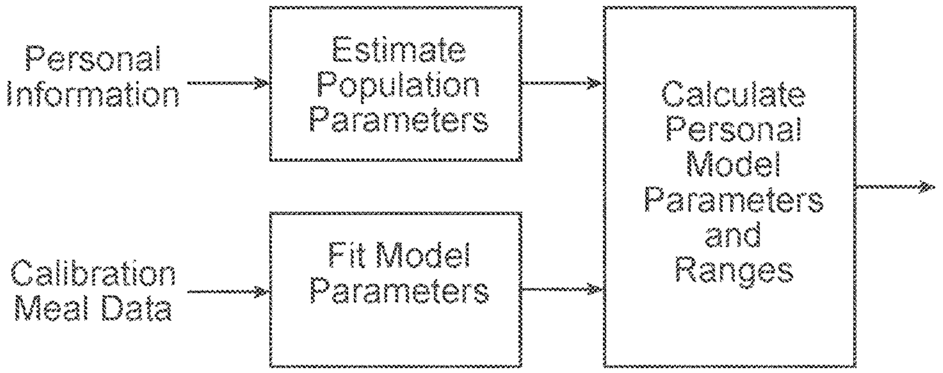
FIG. 2 is a schematic representation of the learning personalized model.

The learning personalized model (step 11 in FIG. 1A) is generally described in FIG. 2.

In a metabolic model the pattern of blood component response to the consumption of a meal is explained biologically through different relationships representing stages in the digestion process. The dependency is defined by a set of parameters, determined by the food nutritional content and the physiological metabolic parameters of the individual.

A compartment pharmacokinetics model is used for describing the way materials are transmitted among the compartments of a system. Each compartment is assumed to be a homogeneous entity within which the entities being modelled are equivalent. For instance, in a pharmacokinetic model, the compartments may represent different sections of a body within which the concentration of a material is assumed to be uniformly equal. In such a metabolic model the pattern of blood component response to the consumption of a meal is explained biologically through different relationships representing stages in the digestion process. The dependency is defined by a set of parameters, determined by the food nutritional content and the physiological metabolic parameters of the individual.

The model in accordance with the invention combines two different metabolic pathways, a "digestion model" that concerns the mechanisms associated with the digestion of a meal and determines the rate of appearance of glucose in the blood, and a "regulation model" that concerns the mechanisms associated with the disappearance of glucose from the blood and is influenced by the regulating hormones insulin and glucagon. Both of these mechanisms influence the measured glucose level in the blood and/or the interstitial fluid.

The Glucose Regulation Model

The learning personalized model of the invention is based on a unique modification of the Bergman Minimal Model. At this step of the method the approximate model parameters unique to each user are estimated. Such parameters include for example Glucose effectiveness, Insulin sensitivity, basal glucose, distributed glucose concentration at time 0, basal insulin, Acute insulin response to glucose, Disposition index, glucose effectiveness at zero insulin, insulin-attributable glucose disposal, β-cell function, Insulin resistance, Insulin action, Apparent volume of glucose distribution. Bergman provides typical normal values and ranges for each of these parameters (Bergman, 1989).

The Bergman Minimal Model was originally developed for Intra-Venous Glucose Tolerance Test (IVGTT), where glucose is directly injected into plasma with rate $R_G$. According to the Bergman Minimal Model the level of the glucose is defined by the following equations:

$$\frac{dG}{dt} = -k_1(G - G_b) - X \cdot G + R_G$$

$$\frac{dX}{dt} = -k_2 X + k_3(I = I_b)$$

Where:

G—plasma glucose [mg/dL]

X—active insulin [Unit-less]

I—plasma insulin [mU/liter]

$R_G$—Blood glucose rate of appearance [mg/dL/min]

$k_1$—glucose effectiveness (may also be designated $S_G$)

$$S_I = \frac{k_3}{k_2} - \text{is an Insulin sensitivity}$$

Gb—is a basal Glucose level [mg/dL]

The insulin model takes into account both endogenous (internal) and exogenous (external) insulin sources.

In a model proposed by Nucci and Cobelli C. ( ) with respect to subcutaneous insulin kinetics, the plasma insulin equation is:

$$\frac{dI}{dt} = -k_4(I - I_b) + \text{gamma} \cdot (G - G_T)^+ t + R_i$$

Where $R_i$ is Insulin Rate of Appearance. It can be calculated using the following model:

$$\frac{dI_{sc1}}{dt} = -(k_d + k_{a1})I_{sc1} + \text{Injection}(t)$$

$$\frac{dI_{sc2}}{dt} = -k_{a2} I_{sc2} + k_d I_{sc1}$$

$$R_i = k_{a1} I_{sc1} + k_{a2} I_{sc2}$$

Where:

gamma-Rate of pancreatic release after glucose bolus $k_4$—This is a rate of insulin clearance Isc1—is the amount of non-monomeric insulin in the subcutaneous space Isc2—is the amount of monomeric insulin in the subcutaneous space.

Ib—basal insulin

While the model can describe any user, there are individual differences in the model parameters which are unique to each user. However, typical ranges for each of the parameters can be assigned to the user based on known population categories. As indicated above, Bergman for example, assigns typical values for Glucose effectiveness and Insulin sensitivity according to certain population subgroups, e.g. white men, healthy women, postpartum pregnancy, aged, high-carbohydrate diet, Mexican Americans, aged ad libitum diet, obese non-diabetic, women on oral contraceptives and non-insulin dependent diabetes.

The Digestion Model

When food is ingested it is subjected to a long series of mechanical and chemical modifications. In the mouth it is mechanically modified by chewing and chemically altered by mixing with saliva, that adds water and enzymes that initiate the breakdown of carbohydrates and proteins. In the stomach bile acids and stomach excretions are added and the gastric motility mixes and divides the food further. Eventually the food is ejected into the small intestine where further water is added or removed, resulting in an approximately equimolar solution. The breakdown and absorption of all digestible components of the food is completed in the small intestine and to a smaller degree in the large intestine, where the food is transported by the peristaltic movements of the intestine. A part of the food leaves the intestine and is excreted as faeces.

The rate at which the stomach ejects its contents into the intestine is determined by several factors, including the composition of the meal, the degree of filling of the stomach and the blood glucose level, as well as the gut absorption rate. Mechanical factors are also important, as liquid components leave the stomach at a higher rate than solid components and small solid components leave at a higher rate than larger solid components. The admixture of water is also important, where the water may either be part of the food ingested, drunk as part of the meal or added as gastric secretion or bile. The filling of the stomach also affects the stomach emptying rate, with a full stomach having a higher emptying rate than an almost empty stomach.

To produce a model, several assumptions and simplifications were made. As a starting point, it was taken that the stomach as a first approximation functions as a constant calorie generator with an ejection rate of 2.3-3.3 kcal/min after a medium sized meal (Maughan and Leiper; Macdonald; Carbonnel et al.). Assuming that differences in the ejection rate between different individuals is proportional to body weight, then the specific emptying rate (SER) per kg body mass (BM) can be written as follows:

$$SER_0[\text{kJ/mm/kg}] = 3.0 * 4.185\ \text{kJ/min}\ BM/70\ \text{kg} + 0.179\ \text{kJ/min/kg}$$

The effect of stomach filling is accounted for by a stomach filling factor, which is assumed to have an logarithmic dependence on the stomach volume. In addition, the effect of blood glucose on the gastric emptying was disregarded, although it should be recognized that hypo- or hyperglycemia may significantly modify the gastric emptying rate. With these assumptions:

$$r_{GUT} = SER_0 \cdot \log(1 + C_H(t) \cdot S_{RAT})$$

Whereby:

$r_{GUT}$—is the gastric emptying rate

Srat—Stomach Rate of Appearance constant.

The metabolic model of the invention combines the above described digestion and glucose regulation models, and includes the following set of equations:

$$\frac{dC}{dt} = -r_{GUT} + \delta_{Carbs}$$

$$\frac{dG_q}{dt} = -k_{abs} \cdot G_q + \frac{r_{GUT}}{V_G \cdot BW}$$

$$R_{G=} - k_{abs} \cdot G_q$$

Whereby

δCarbs—is the amount of carbs consumed during the time step $k_{abs}$—absorption constant $V_G$—is the effective volume of the glucose compartment (per kg of body weight)

BW—user bodyweight $R_G$—is the glucose rate of appearance in plasma.

Using this model the response to different amounts of carbohydrates with the same meal type can be accurately predicted as well as the response to other meal types by modifying the other model parameters.

Figure 3:
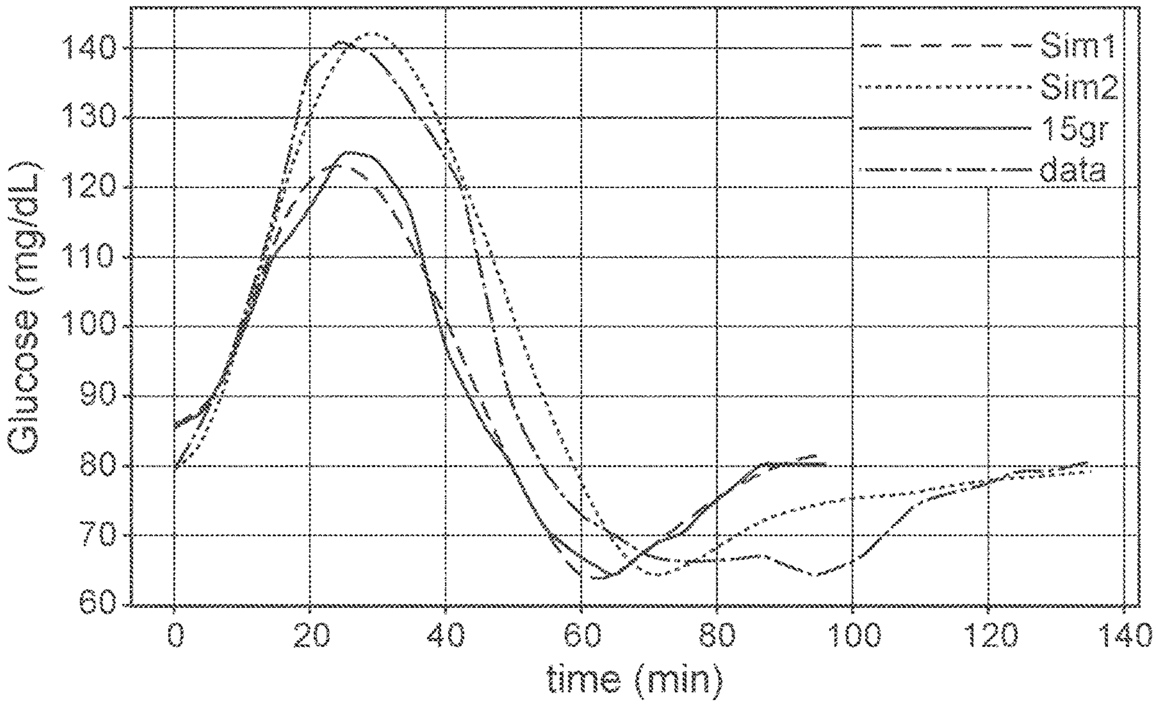
FIG. 3 is a graph showing the prediction of the glucose response to a 30 gr glucose meal after learning the individual model parameters from 15 gr test meal.

As can be seen in FIG. 3 the glucose response to a 30 gr glucose meal was accurately predicted after learning the individual's model parameters from a 15 gr test meal.

To summarize this step, based on the personal information each user is assigned to a specific population group, for example the population groups listed above. The user is thereby assigned with general estimated parameter value ranges (also termed herein "a general value range") for each of said personalized metabolic parameters according to known values in a population appropriate for this population group. —

In addition, after the calibration meal data is received, the model parameter set that gives the best fit to the observed results is identified.

Namely, the calibration meal data is analyzed to find the best fit to the model parameter estimates using a response graph fit, thereby obtaining a value range for each of said personalized metabolic parameters which is specific to the individual that consumed the calibration meals, also termed herein "a specific value range".

Preferably, the specific value range is smaller than the general value range.

A non-limiting example of a fitting technique is the Levenberg-Marquardt least squares algorithm (see FIG. 4).

The data from both the personal information and the individual calibration is used to calculate personal model parameters and ranges. In one embodiment, a weighed averaging technique is used to take into account data from both sources.

The Training Procedure

Next, the personalized metabolic parameter values and ranges are incorporated into a training procedure.

The training procedure will now be further explained (with reference also to FIG. 1A). The training procedure comprises the following steps:

a. Generating multiple virtual data sets comprising:
   (i) metabolic parameters that fall within the personalized metabolic parameter value ranges obtained using the learning personalized metabolic model (step 12 in FIG. 1A); and
   (ii) data indicative of a plurality of meal scenarios and/or insulin injection scenarios;
b. Generating an output virtual data set that includes data indicative of daily virtual levels of the biomarker (e.g. glucose) based on the personalized metabolic parameters obtained using the learning personalized metabolic model.

The training procedure further includes training a Machine Learning (ML) system including:

c. Filtering the output virtual data set data obtained in (b) to produce estimates for unknown variables (e.g. by using a Dual Unscented Kalman Filter) (step 13 in FIG. 1A); and d. Inputting the estimates for unknown variables to a machine learning system (step 14 in FIG. 1B).

Each of these steps will now be described in detail.

Generation of Virtual Data Sets

At the next stage a large amount of virtual data sets are generated. These virtual data sets will be used to train the algorithm.

Figure 5:
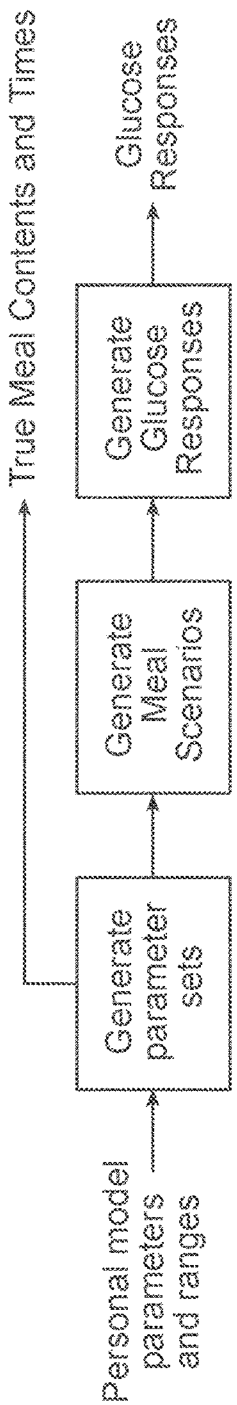
FIG. 5 is a schematic representation of the Generation of virtual datasets.

The generation of the virtual data sets is generally described in FIG. 5.

A first virtual data set comprises a large amount of virtual nutritional information, i.e. virtual daily meal scenarios.

The virtual nutritional information refers to about 4 meals per day for about 20,000, 25,000, 30,000 or more days. For example 25,000 days. Namely the virtual nutritional information refers to about 80,000, 100,000, 120,000 or more mdaily meal scenarios. Generally, the carbohydrate content in a meal is between 0 and 200 grams. These meal scenarios are generated randomly and generally represent typical nutritional diversity in day to day food consumption.

The individual parameters and ranges from the previous step are used to generate a second virtual data set. Accordingly, multiple parameter sets are generated having mean values and ranges calculated based on the personal model parameters and ranges previously obtained. Uniform or gaussian parameter distribution may be used.

In some embodiments said parameter sets that fall within the personalized metabolic parameter value ranges are random parameter sets.

In some embodiments, said plurality of meal scenarios and/or insulin injection scenarios is a plurality of random meal scenarios and/or insulin injection scenarios.

In a specific embodiment, wherein the individual is a diabetic patient, a virtual data set comprising insulin injection scenarios is also generated.

Finally, daily glucose responses are calculated (constituting an example of output virtual data set) using the personalized metabolic model based on the virtual metabolic parameters and virtual meal (and/or insulin injection) scenarios generated as described above.

Optionally, sensor noise may be compensated for according to available models known in the art.

In some embodiments, each consumed meal is associated with a time tag, namely an indication showing the approximate start time and completion time of the consumed meal. Accordingly, in some embodiments the calculated daily glucose responses, as well as other metabolic state parameters such as C, Gq, Ra are used to detect the beginning and end of a meal. Meal-time detection can therefore be performed in several ways, for example, but not limited to:

Detecting when the intake prediction is above certain threshold for several consecutive time steps; or employing a pattern recognition algorithm than can detect intake patterns such as Linear Discriminant Analysis or any other pattern recognition algorithm.

Figure 1B:
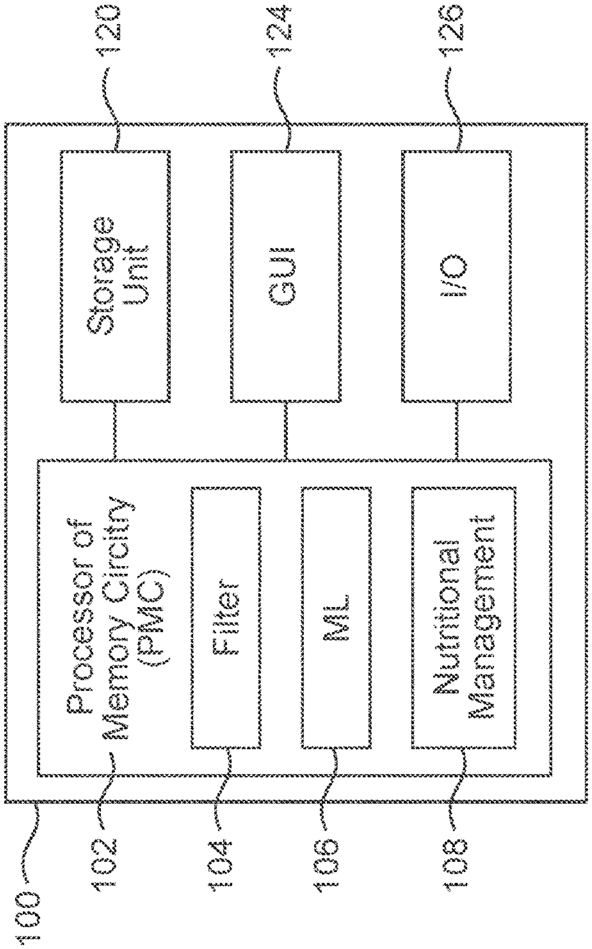
FIG. 1B illustrates schematically a block diagram of a computerized system capable of training and/or using a Machine Learning (ML) system for nutritional analysis and possibly nutritional management, in accordance with certain embodiments of the invention.

Before moving on to describe the computational stages of training the ML system (steps 13 and 14 in FIG. 1A), there will be a detailed description of FIG. 1B illustrating schematically a block diagram of a computerized system capable of training and/or using a Machine Learning (ML) system for nutritional analysis and possibly nutritional management, in accordance with certain embodiments of the invention.

Thus, the system 100 illustrated in FIG. 1*b* is a computer-based system for training or using a machine learning (ML) system 106. The ML system 106 is configured for outputting nutritional analysis data and facilitates utilizing these data and possibly other for nutritional management through nutritional management system 108 operably connected thereto. The ML system is operably connected to filtering system 104 (e.g. implementing Kalman Filter—all is will be described in greater details below with reference to FIG. 6), The latter will be explained in greater details blow with reference to steps 13 and 14 of FIG. 1A. Note that system 100 may be configured to train the ML system and once duly trained for or use of the ML system for its designated purpose using it, all as is explained in greater details herein.

In some cases, the training dataset can be obtained from a local storage unit 120 which comprises an database 122 configured to store set of personalized machine learning parameter values and/or set of personalized filter parameter values, all as will be explained with reference to FIG. 9 below, and/or other data that may be relevant for training or usage of the system of the invention. In some other cases, the specified data or portion thereof can reside external to system 100, e.g., in one or more external data repositories, or in an external system or provider that operatively connect to system 100, and the specified data can be retrieved via a hardware-based I/O interface 126.

As illustrated, system 100 can comprise a processing and memory circuitry (PMC) 102 operatively connected to the I/O interface 126 and the storage unit 120. PMC 102 is configured to provide all processing necessary for operating system 100 which is further detailed with reference to FIGS. 1A, 6 8 AND 9. PMC 102 comprises a processor (not shown separately) and a memory (not shown separately). The processor of PMC 102 can be configured to execute several functional modules in accordance with computer-readable instructions implemented on a non-transitory computer-readable memory comprised in the PMC. Such functional modules are referred to hereinafter as comprised in the PMC. It is to be noted that the term processor referred to herein should be expansively construed to cover any processing circuitry with data processing capabilities, and the present disclosure is not limited to the type or platform thereof, or number of processing cores comprised therein.

In certain embodiments, functional modules comprised in the PMC 102 can comprise a filter system 104 an ML system 106 and nutritional management system 108. The functional modules comprised in the PMC may be operatively connected with each other. The interoperability between the respective systems will be described in greater details with reference to FIGS. 1A, 6 8 and 9 below.

The I/O interface 126 can be configured to obtain, as input, data such as output virtual data sets (e.g. data indicative of virtual glucose levels in training mode, or data indicative of measured glucose levels in daily usage mode) that may include data indicative of a set of virtual biomarker (e.g. glucose) levels in training mode or data indicative of measured biomarker (e.g. glucose) levels in daily usage mode from storage unit/data repository or external unit such as virtual data set generation system 12 (see FIG. 1A), and provide, through the I/O interface as output data such as nutritional analysis data and/or nutritional management data Optionally, system 100 can further comprise a graphical user interface (GUI) 124 configured to render for display of the input and/or the output (such as the specified nutritional analysis data and/or nutritional management data) to the user. Optionally, the GUI can be configured to enable user-specified inputs for operating system 100.

Once trained, the ML system, can be used to output nutritional analysis data and possibly utilizing these data for processing and outputting nutritional management data, all as explained herein.

It is also noted that the system illustrated in FIG. 1B can be implemented in a distributed computing environment, in which the aforementioned functional modules shown in FIG. 1B can be distributed over several local and/or remote devices, and can be linked through a communication network.

Those versed in the art will readily appreciate that the teachings of the presently disclosed subject matter are not bound by the system illustrated in FIG. 1B; equivalent and/or modified functionality can be consolidated or divided in another manner and can be implemented in any appropriate combination of software with firmware and hardware. The system in FIG. 1B or at least certain components thereof can be a standalone entity, or integrated, fully or partly, with other entities. Those skilled in the art will also readily appreciate that the data repositories or storage unit therein can be shared with other systems or be provided by other systems, including third party equipment.

According to certain embodiments, non-transitory computer-readable memory comprised in the PMC.

Figure 6:
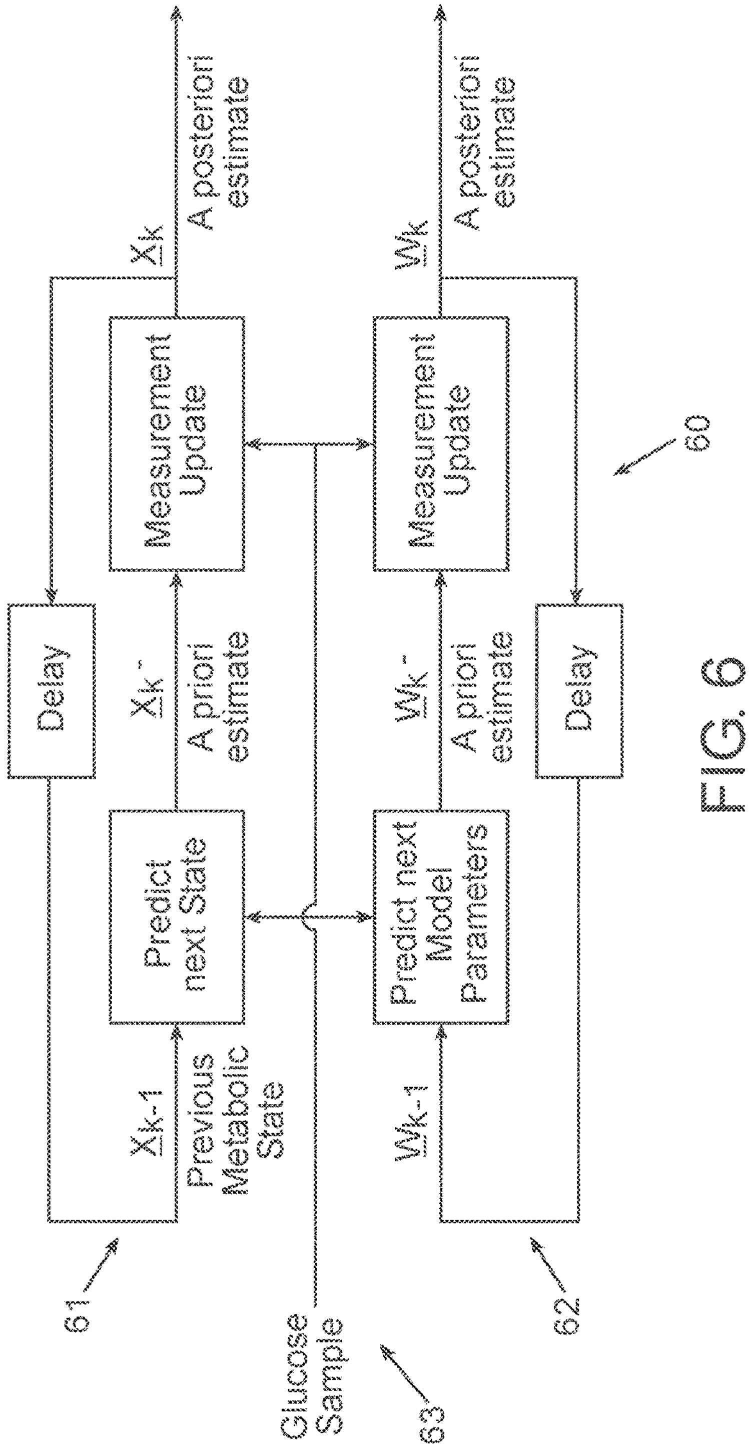
FIG. 6 illustrates schematically a block diagram of a Kalman Filtering used in a computerized system, in accordance with certain embodiments of the present invention.
Figure 7A:
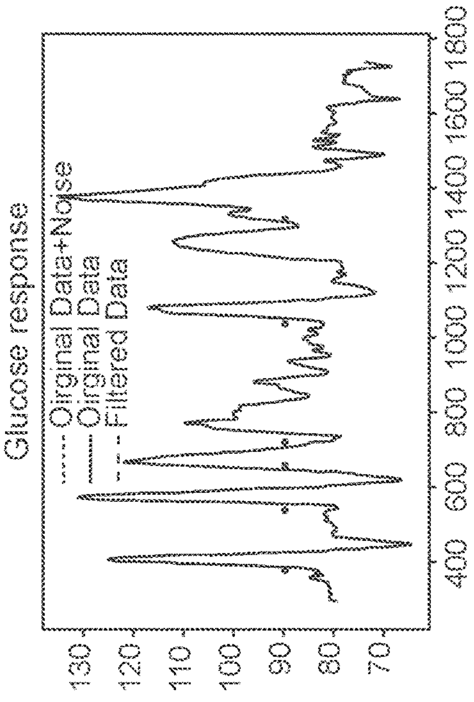
FIGS. 7A, 7C, 7E and 7G are graphs showing results of the variables estimation during the everyday use phase with real measured CGM data: 7A—glucose response; 7C—Gq data; 7E—intake estimation data; and 7G—insulin response.
Figure 7B:
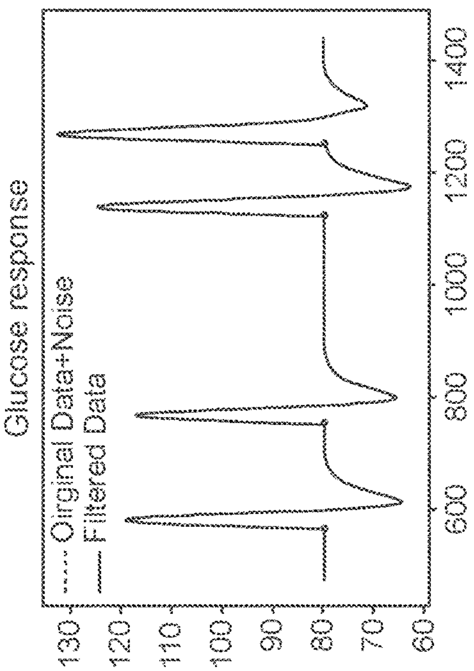
FIGS. 7B, 7D, 7F and 7H are corresponding graphs showing variable estimation results obtained during the training phase: 7B—glucose response; 7D—Gq data; 7F—intake estimation data; and 7H—insulin response.
Figure 7C:
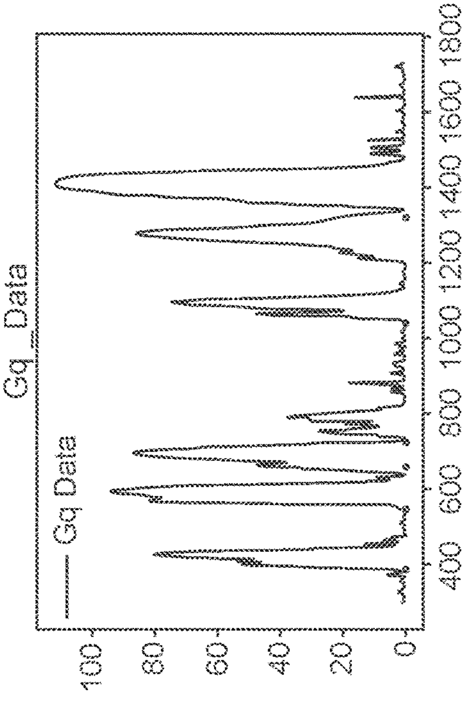
Figure 7D:
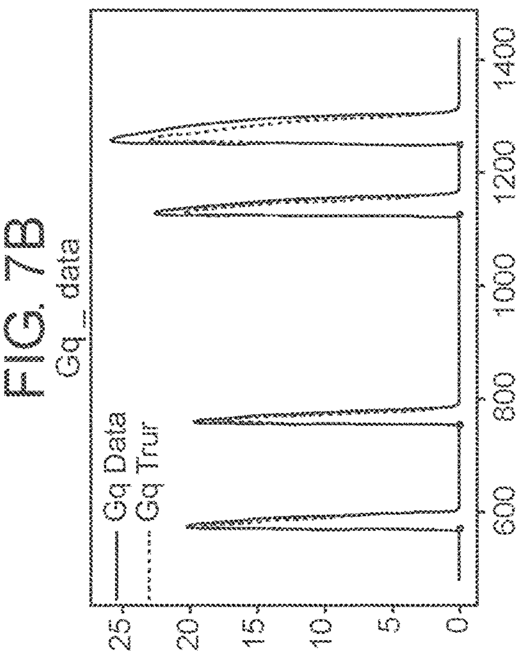
Figures 7E, 7F, 7G, 7H:
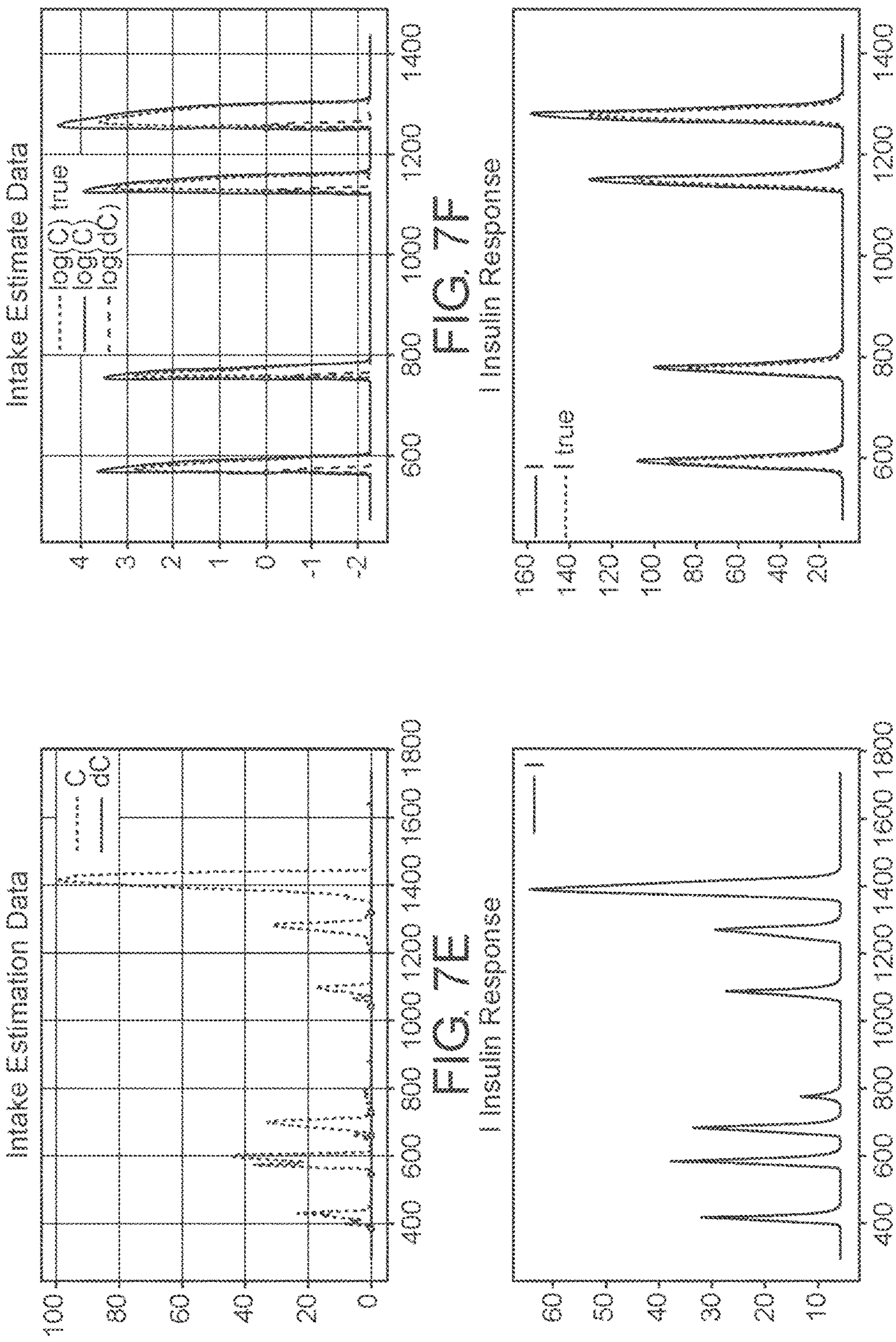
Figure 9:
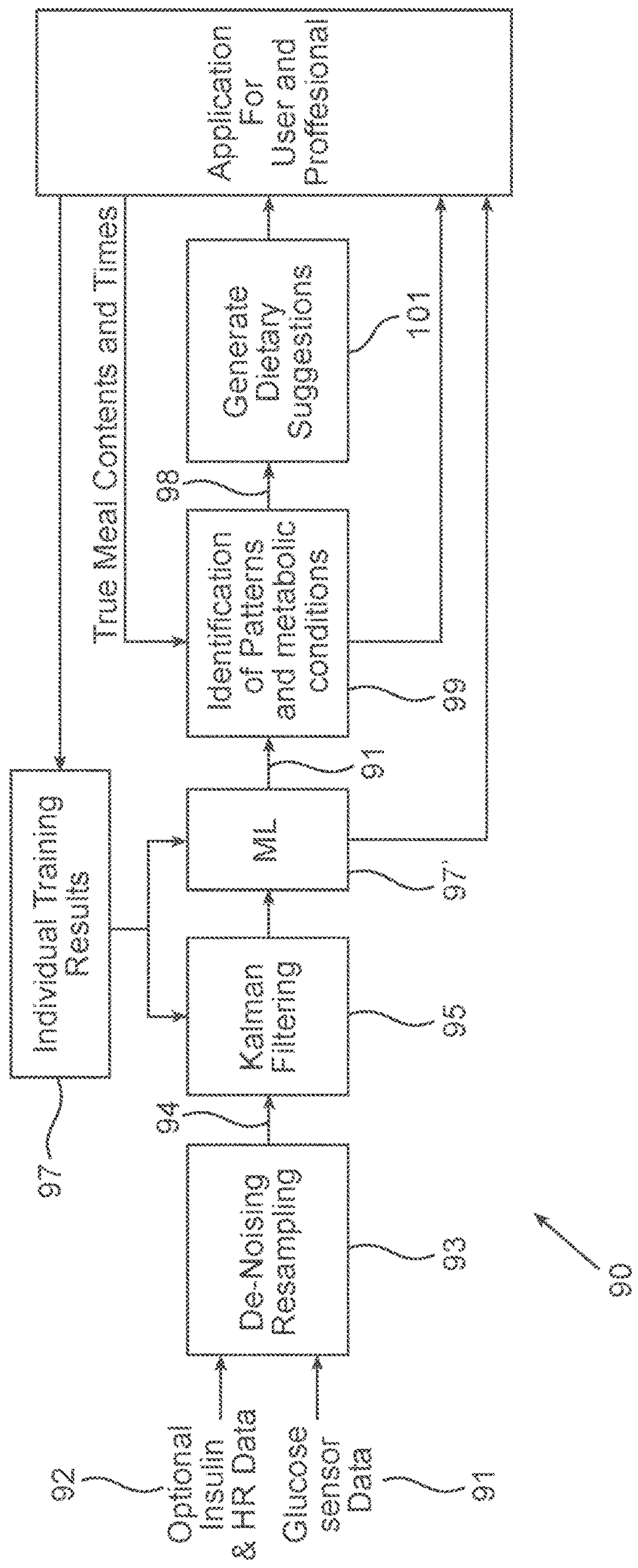
FIG. 9 illustrates schematically a sequence of operation of using a machine learning system for nutritional analysis and possibly nutritional management, in accordance with certain embodiments of the present invention.

While not necessarily so, the process of operation of system 100 can correspond to some or all of the stages of the computational stages described with respect to any of FIGS. 1A, 6 and 9. Likewise, the computational stages described with respect to any of FIGS. 1A, 6 and 9. and their possible implementations can be implemented by system 100. It is therefore noted that embodiments discussed in relation to the methods described with respect to any of FIGS. 1A, 6 and 9. 2-3 can also be implemented, mutatis mutandis as various embodiments of the system 100, and vice versa.

Bearing in mind attention is reverted to FIG. 1A and in particular to computational stages 13 and 14. Thus, Filtering Stage (Step 13)

The individual metabolic information according to the model of the invention includes metabolic parameters which cannot be measured in a continuous manner or are otherwise unavailable. According to certain embodiments of the method of the invention only the blood or subcutaneous glucose level is measured (or virtually generated as discussed above) (termed G in the regulation model described above) and can be used as input, while other metabolic information is unavailable. The unavailable parameters are, for example, the glucose or carbohydrate content in other compartments (e.g. the stomach, gut), active insulin, plasma insulin (termed X and I in the regulation model described above), carbohydrates intake during the last time step (e.g. 1 minute to 5 minutes) (dC), insulin injection during the last time step (dI), plasma glucose concentration (G), and the amount of non-monomeric and monomeric insulin in subcutaneous compartments (Isc1/Isc2).

In order to obtain the lacking information a filtering tool may be employed.

In one embodiment, said filtering tool is Dual Unscented Kalman Filter (UKF). UKF being an example of a filter system 104 that utilizes PMC 102.

Note that while for convenience the description is exemplified with reference to Dual UKF, this is only an example. Other non-limiting examples being Single UKF, Extended Kalman Filter (EKF), or others all as known per se.

Note also that filtering may include a known pre-processing stage of cleaning the signal such as de-noising, Resampling and so forth.

The UFK, may be used in both training stage and once trained also in regular daily use. Note that the description herein focused on the training stage.

The UKF can recover the information that is not directly measurable based on the physiological fact that all compartments influence each other. In accordance with certain embodiments as a result a complete information set concerning all of the model's compartments can be obtained even without performing direct measurements.

The UKF algorithm uses a series of measurements observed over time, containing statistical noise and other inaccuracies, and produces data indicative of Estimates of unknown variables that tend to be more accurate than those based on a single measurement alone, by estimating a joint probability distribution over the variables for each timeframe.

Typical yet not exclusive list of data indicative of estimates of unknown variables may include at least one of: carbohydrates intake during the last time step (dC), insulin injection during the last time step (dI), carbohydrates amount in stomach compartment, Carbohydrates amount in the gut compartment (Gq), plasma glucose concentration (G), active insulin (X), plasma insulin (I) and the amount of non-monomeric and monomeric insulin in subcutaneous compartments (Isc1/Isc2).

During the training phase, The UKF works in a two-step process. In the prediction step, the Kalman filter produces estimates of the current state variables along with their uncertainties and utilizes inputs. The inputs may be provided from the previous virtual data set generation system (see e.g. 12 in FIG. 1) and may include data indicative of virtual Glucose levels that were generated in response to feeding data indicative of virtual meals. Once the outcome of the next virtual measurement (necessarily corrupted with some amount of error, including random noise) is observed, and based also on corresponding virtual data set sample (e.g. data indicative of virtual Glucose level) these estimates are updated using a weighted average, with more weight being given to estimates with higher certainty. The algorithm is recursive. It can run in real time, using only the input (e.g. virtual glucose measurement) and the model predicts the next measurement. In certain embodiments a "memory" is used, e.g. the input is last N samples. No additional past information is required. The training is performed with respect to a given subject whilst feeding to the UKF virtual datasets including (e.g. data indicative of Glucose level) that were generated in response to data indicative of virtual meal. The latter, as may be recalled were generated using the learning personalized metabolic model that was trained to adapt to this particular subject, all as discussed in detail above. Note that in accordance with certain embodiments the second stage is the update stage, after prediction of the next measurement based on model parameters it is compared with the actual virtual measurement. The final output is a weighted average between both, and also some modification to other metabolic parameters based on the error between predicted and virtual measured values. These estimates are updated using a weighted average.

Once the estimates of the UFK converge, namely the UFK is able to produce the estimates of unknown variables at desired accuracy for this particular subject, the internal coefficients/weights of the UFK may be stored e.g. in storage unit 120, for use by system 100 in a later stage of utilizing the system (on regular e.g.—possible daily use) for determining, based on measured data (such as measured glucose level) the pertinent nutrition analysis which may include the determination of the consumed Carbs and possibly the meal time, as well as personal health parameters (for example insulin/glucose sensitivity in diabetic patients) all as will be discussed in greater detail with reference to FIG. 9.

The specified internal coefficients/weights constitute an example of a set of personalized filter parameter values that characterize the subject.

The Unscented Kalman filter (UKF) uses a deterministic sampling technique known as the unscented transformation (UT) to pick a minimal set of sample points (called sigma points) around the mean and calc. The sigma points are then propagated through the nonlinear functions, from which a new mean and covariance estimate are then formed.

The dual estimation problem consists of simultaneously estimating the clean state and the model parameters from the noisy data. This can be achieved by using for example two UKF filters (designated collectively as 60), one for state estimation (61) and one for parameters estimation as presented (62) in FIG. 6. Note that the input dataset is fed through input (63), e.g. virtual Glucose level samples and the estimates of unknown variables will be outputted in 64 (where $X_K$ stands for the estimate of unknown variable such as s—G, dC, Gq, X, I, Isc1/Isc2, and $W_K$ stands for the parameters estimation (forming part of estimates of unknown variable) such as k1-k4, ka1, ka2, ser0, srat, gamma.

The following is an example of state prediction function according to the model of the present invention. Note that the example below is provided for illustration purposes only and is by no means binding:

The estimated metabolic state at step k−1 (time $t_{k-1}$) is given by:

$$\underline{X}_{k-1} = \left[C^{k-1}, G_q^{k-1}, G^{k-1}, X^{k-1}, I^{k-1}, I_{sc1}^{k-1}, I_{sc2}^{k-1}\right]$$

The metabolic parameters are:

$$\underline{W}_{k-1} = \left[\gamma^{k-1}, G_b^{k-1}, I_b^{k-1}, G_T^{k-1}, k_1^{k-1}, k_2^{k-1}, k_3^{k-1}, k_4^{k-1}, SER_0^{k-1}, V_G^{k-1}, S_{RAT}^{k-1}, k_{abs}^{k-1}, k_d^{k-1}, k_{a1}^{k-1}, k_{a2}^{k-1}\right]$$

The a priori estimate of the next metabolic state in the predict stage is $$\underline{X}_k^- = \underline{X}_{k-1} + d\underline{X}_k$$

Where:

$$\underline{dX}_k = \left[dC^k, dG_q^{k-1}, dG^k, dX^k, dI^k, dI_{sc1}^k, dI_{sc2}^k\right]$$

and is given explicitly by:

$$dI_{sc1}^k = -(k_d^{k-1} + k_{a1}^{k-1}) \cdot I_{sc1}^{k-1} + \frac{\delta_{Insulin}^k}{V_I^{k-1} BW}$$

$$dI_{sc2}^k = -k_{a2}^{k-1} \cdot I_{sc2}^{k-1} + k_d^{k-1} \cdot (I_{sc1}^{k-1} + dI_{sc1}^k)$$

-continued $$r_{GUT}^k = SER_0^{k-1} \cdot \log(1 + C^{k-1} \cdot S_{RAT}^{k-1})$$

$$dI^k = -k_4^{k-1} \cdot (I^{k-1} - I_b^{k-1}) + \gamma^{k-1} \cdot (G^{k-1} - I_b^{k-1}, G_T^{k-1})(t - t_0) + k_{a1}^{k-1} \sim (I_{sc1}^{k-1} + dI_{sc1}^k) + k_{a2}^{k-1} \cdot (I_{sc2}^{k-1} + dI_{sc2}^k)$$

$$dC^k = -r_{GUT}^k + \delta_{Carbs}^k$$

$$dG_q^k = -k_{abs}^{k-1} \cdot G_q^{k-1} + \frac{r_{GUT}^k}{V_G^{k-1} \cdot BW}$$

$$dX^k = k_3^{k-1} \cdot (I^{k-1} + dI^k - I_b^{k-1}) - k_2^{k-1} \cdot X^{k-1}$$

$$dG^k = -k_1^{k-1} \cdot (G^{k-1} - G_b^{k-1}) + (X^{k-1} + dX^k) \cdot G^{k-1} - k_{abs}^{k-1} \cdot (G^{k-1} + dG_q^k)$$

With the initial conditions:

$$\left[C^0, G_q^0, G^0, X^0, I^0, I_{sc1}^0, I_{sc2}^0\right] = [0, 0, 90, 0, 9, 0, 0]$$

For the parameters, we assume that the parameters value remains fixed over time, therefore a priori prediction is:

$$\underline{W}_k^- = \underline{W}_{k-1}$$

The initial condition are determined according to calibration information provided.

At the update stage the glucose estimation is compared using the predicted a priori values vs the actual measured glucose sample—$G_k$. Error is defined as:

$$e_k = \underline{X}_k^-[3] - G_k$$

Where $$\underline{X}_k^-[3]$$

refers to the third vector component, e.g. a priory estimation of the glucose value at the step k.

The final values after update stage are:

$$\underline{X}_k = \underline{X}_k^- + \underline{K}_X \cdot e_k$$

$$\underline{W}_k = \underline{W}_k^- + \underline{K}_W \cdot e_k$$

Where $\underline{K}_X$ and $\underline{K}_W$ are Kalman gain, calculated according to the algorithm presented in UKF literature.

The inputs to the algorithm:

$$\delta_{Carbs}^k$$

is the amount of carbs consumed at the step k $$\delta^{k}_{Insulin}$$

is the amount of carbs consumed at the step k $G_k$—is the virtually generated glucose response These vectors are generated as a part of virtual dataset generation procedure.

Note that the invention is by no means bound by the specified Kalman Filter (UKF) system and accordingly other known per se solutions may be Representative results of Dual UKF filter working on real and virtual data are presented in FIG. 7. FIG. 7 presents the action of the UKF in the various phases during system operation. Graphs B, D, F and H present variable estimation results obtained during the training phase on one of the vectors of the virtual dataset: 7B—glucose response; 7D—Gq data; 7F—intake estimation data; and 7H—insulin response. Graphs A, C, E and G present results of the variables estimation during the everyday use phase with real measured CGM data: 7A—glucose response; 7C—Gq data; 7E—intake estimation data; and 7G—insulin response.

In specific embodiments, wherein the subject is a diabetes patient suffering from IDDM and receiving insulin injections, the insulin injections are regarded as an input in both the training stage of the method and the day to day implementation. The insulin injections are used in the training algorithm for reevaluating the metabolic state.

For example, the amount of insulin delivered to the patient by insulin injections or by an insulin pump is known and may be used as input to the Kalman filter. In certain embodiments whereby there is no information on the amount of insulin delivered, the system makes an estimation of this parameter in a similar manner as any other unknown variable. In such case, the estimation of delivered insulin becomes another output of the method that can be helpful in treatment.

Inputting Filtered Data and Using it for Training a Machine Learning System (Stage 14)

Having described the filter step, there follows a description of the Inputting Filtered Data and Using it for Training a Machine Learning System step (14 in FIG. 1A).

As a next step a machine learning (ML) system is trained to perform nutritional analysis, e.g. to detect meals and contents and possibly meal time using the recovered metabolic states and parameters possibly together with known meal and insulin scenario data. Note that in accordance with certain embodiments, the ML system utilizes a so called True Meals Contents and (optionally) their corresponding Meal Times that will be fed to the Machine leaning (stage 14) based on virtual meal data outputted from stage 12 (Generation Virtual Dataset step). The True meal data will serve as a reference data to the ML system to determine (during training phase) whether its predicted nutritional analysis (that includes retroactive determination of the consumed Carbs) matches the reference true meal data (that may include data indicative of consumed Carbs), and update the ML internal parameters accordingly, until the prediction is sufficiently accurate. Nutritional analysis and accordingly the true data may apply mutatis mutandis also to other data such as e.g. Insulin related data.

In one embodiment, the training step is implemented by Machine Learning (ML) system 106 that utilizes PMC 102 (see FIG. 1B).

The ML system, may be used in both training stage and once trained also in regular daily use. Note that the description herein focused on the training stage.

The ML system 106 may be in accordance with certain embodiment a known per se Convolutional neural network (CNN), a class of deep neural networks, is used. The CNN is a multilayer fully connected layer neural network that uses a convolution tool in order to process information over some particular time window, assign importance (learnable weights and biases) to various aspects/objects in the data and be able to detect and differentiate patterns.

In accordance with certain embodiments, the ML is of a type known as: Supervised Learning. In a supervised learning approach, the system uses a dataset of observations with labelled outcomes. Examples of supervised learning algorithms that may be used in the model development process: ordinary least squares regression, logistic regression, least absolute shrinkage and selection operator (LASSO) regression, ridge regression, elastic net regression, linear discriminant analysis, Naïve Bayes classifiers, support vector machines, Bayesian networks, a variety of decision trees especially Random Forests and AdaBoost or gradient boosting classifiers, artificial neural networks such as Convolutional Neural Networks (CNN) or Recurrent Neural Network (RNN) and ensemble methods.

In accordance with certain other embodiments Un-Supervised Learning ML model may be used In a unsupervised learning approach, the system uses a dataset of observations without labelled outcomes. The optimization criteria in this approach can be for example matching eating pattern on the specific meals, days, weeks, or other general optimization criteria, all as known per se.

This dataset is used in the specified training phase of the ML as discussed herein to develop a model that estimates future nutritional content of meals, based on measurement of features and knowledge of user parameters.

In some embodiments, the following parameters of the CNN are used. The listed below parameters/examples are provided for illustration purposes only and are by no means binding:

The first 3 components of the estimated state vector $$X_k\left(C^{k-1}, G_q^{k-1}, G^{k-1}\right)$$

are passed via 7 layers convolutional network. The first 4 layers work on each component separately. The layers structure is:

layer1: Convolution Layer: filters=10, kernel size=9, activation=ReLU layer2=Pooling Layer: pool size=3 layer3=Convolution Layer: filters=10, kernel_size=7, activation=ReLU layer4=Pooling Layer: pool_size=3

While the remaining 3 layers work on the resulting features from the 3 signals jointly. The layers structure is:

layer5=Convolution Layer: filters=10, kernel_size=5, activation=ReLU layer6=Convolution Layer: filters=20, kernel_size=9, activation=None layer7=tf.keras.layers.ConvID(filters=1, kernel_size=1, activation=None Where:

ReLU=rectified linear unit

The output of this vector is the signal that represents the estimated intake at the time step k. To optimize the parameters of the described neural network, we compare this output to the reference data provided. This way, network parameters optimization in achieved.

Figure 8:
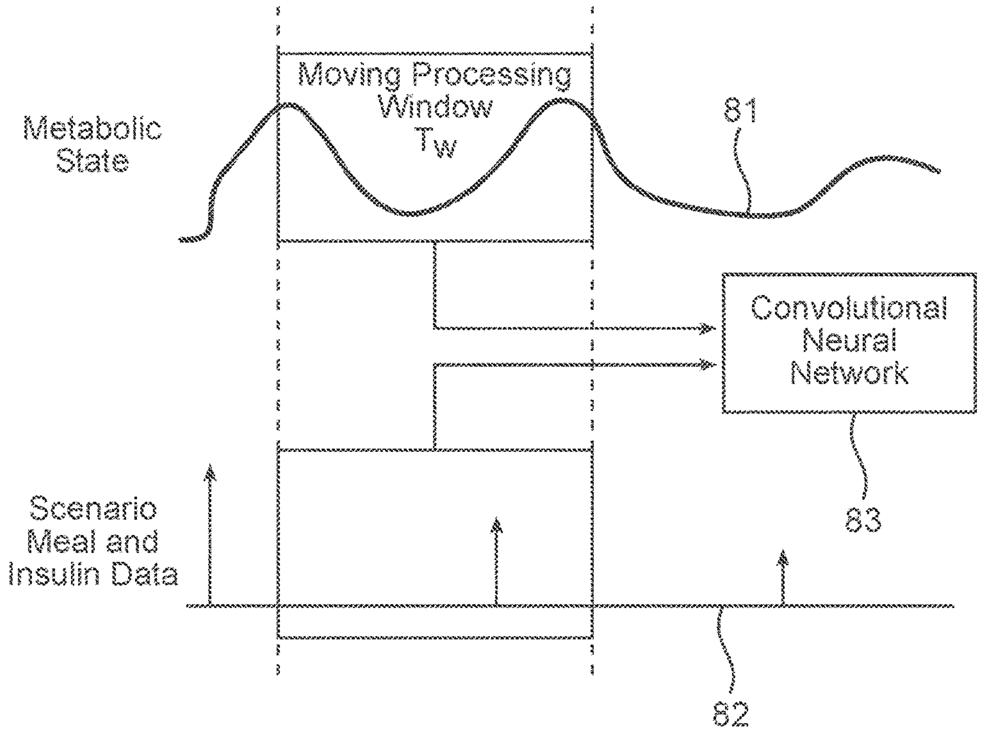
FIG. 8 is a simplified graphic representation of a training set used for training machine learning system, in accordance with certain embodiments of the present invention.

Attention is now drawn to FIG. 8, illustrating a simplified graphic representation of a training set used for training machine learning system. The graph illustrates for simplicity only a single estimated unknown variable spread over time, termed here "Metabolic state" (81) (the "metabolic state" variable includes any of the unknown variables as indicated above, for example but not limited to, carbohydrates amount in stomach compartment, Carbohydrates amount in the gut compartment (Gq), plasma glucose concentration (G), active insulin (X), plasma insulin (I)) as well as the corresponding meal (and Insulin) data (82), that constitute a training set are fed to a ML system of the CNN type 83 (see also 106 in FIG. 1B). The ML system is capable of learning after being provided with sufficient samples to correlate the input training data (being derived from virtual Glucose level that were outputted by the virtual dataset Generation system—all as discussed above). Once duly trained and as will be discussed below, the system can be used for regular use, as will be explained with reference to FIG. 9, below.

Note that in accordance with certain embodiments of the computerized system/method of the invention a relatively large number of virtual computer generated meals are utilized compared to a smaller number of real meals. This feature constitutes an advantage in that notwithstanding that only few real meals are used (with the obvious burden posed on the treated subject that needs to consume them) the ML system is adequately trained utilizing the virtual meals data (which do not pose any burden on the subject since the meals are automatically generated). The net effect is thus that notwithstanding that only few real meals are used, the model is trained accurately and efficiently and allows to obtain qualitative nutritional analysis and consequently qualitative nutritional management.

Everyday Operation—

Attention is drawn to FIG. 9 illustrating schematically a sequence of operation of using a machine learning system for nutritional analysis and possibly nutritional management, in accordance with certain embodiments of the present invention.

As shown in FIG. 9, after training the ML system as discussed above, the system is used for managing a subject's nutrition in an everyday operation mode.

Thus, the data collected from the biosensors, is transmitted to an application on a smartphone device, or other mobile device with similar communication, display and processing capabilities. The user and/or their dietician logs into the application personal parameters of the user as calculated in the training stage. The user and/or their dietician may define dietary restrictions and goals, in the application through a web-based or a mobile application/user interface. Those specifications may be: recommended consumption amounts of carbohydrates, recommended times of meals, and/or a recommended number of meals per day.

The routine operation of the system may include: running the computerized system of the invention on the data continuously collected from the biosensors, for measurement of carbohydrates consumed per every meal and displaying to the user the amounts consumed, for example: in grams after every meal, as a percentage of total daily recommended consumption after every meal, or at predefined times during the day.

With reference to FIG. 9 in sequence (90), measured data (e.g. measured Glucose level (91) and optionally Insulin level (92) of a given subject as sampled from a Biosensor (not shown) is fed to a known per se De-noising and Resampling (93)—(e.g. resampling using spline data interpolation, Denoising using averaging and SavGol filters) and therefrom (94) is fed to UKF system (e.g. 104 of FIG. 1B) for undergoing filtering (95) in the manner described in detail with reference e.g. to FIG. 6 above. A corresponding set of unknown variables is outputted (96) from the filtering stage. Note that the given subject has undergone training using system (100) and her set of personalized filter parameter values (that were determined in the training phase) and which characterize the subject are a priori fetched (97) (e.g. from storage unit 120—which may form part of the application—e.g. stored in the subject's cellular device) and used in the specified filtering stage (95) thereby securing that accurate set of estimated unknown variables that are relevant for this particular subject are outputted 96 from the filtering stage. The latter data is fed to ML 97 e.g. of CNN type discussed above (see e.g. ML system 106 of FIG. 1B) for outputting (98) the nutritional analysis data relevant for this particular subject. Note that the ML was trained for this particular subject, all as discussed in detail above and the corresponding set of personalized machine leaning parameter values (that were determined in the training phase) and which characterize the subject are a priori fetched (97) and fed to the ML. The nutritional analysis data may include the amount of Carbs that the subject as consumed and possibly the meal(s) time.

There follow a stage of nutritional management (see 108 in FIG. 1B) which by non-limiting example may include the following non-limiting stages: in stage 99 the system notifies the user on deviation from recommended daily carbohydrate consumption. The system may provide special notifications to the user on unusual, unexpected or not recommended meals during the day. The system may provide the user with recommendations on the content of next meals in order to balance (stage 901), compensate and meet daily recommended consumption limits. Based on data collected and processing performed, the system may initiate provision or generate upon request: a periodic personalized analysis of the user's health and dietary condition. The analysis may include: detection of nutritional patterns such as: impulsive eating, eating at non-recommended hours, unbalanced meals and the like. The nutritional management may also include estimation of metabolic parameters such as: Glucose Sensitivity and Insulin Resistance which are indicative of associated health risks such as: Diabetes, Pre-Diabetes or heart diseases. From time to time the system may request the user for information on a certain meal for improvement of prediction performance and better estimation of nutritional trends. A physician or dietician of the user can access the user's data through a web interface and monitor their progress, during the diet period, detect habits that hinder the achievement of dietary goals, detect health risks, and modify or update diet recommendations and limitations. The invention is of course not bound by these specific examples.

A UI system (e.g. 124 of FIG. 1B) for the user and the dietician or physician, which is based on a mobile application and a cloud service, which includes at least one, or any combination of the following features, for example: a UI for logging user's physiological parameters and dietary limitations, a display of carbs and/or fats and/or protein and/or calories consumption per meal and from the beginning of day, week or any period of time, notifications on unusual, unexpected or unrecommended meals, recommendation on next meals in the day to meet dietary personal regime, periodic analysis reports on nutritional patterns, metabolic parameters and health risks.

The system of the invention can be implemented using wearable devices and/or mobile phones.

In the detailed description, numerous specific details are set forth in order to provide a thorough understanding of the invention. However, it will be understood by those skilled in the art that the presently disclosed subject matter may be practiced without these specific details. In other instances, well-known methods, procedures, components and circuits have not been described in detail so as not to obscure the presently disclosed subject matter.

Unless specifically stated otherwise, as apparent from the following discussions, it is appreciated that throughout the specification discussions utilizing terms such as "obtaining", "capturing", "training", "filtering", "generating", "performing", "updating", "providing", "detecting", "receiving", "determining", "processing" or the like, refer to the action(s) and/or process(es) of a computer that manipulate and/or transform data into other data, said data represented as physical, such as electronic, quantities and/or said data representing the physical objects. The term "computer" should be expansively construed to cover any kind of hardware-based electronic device with data processing capabilities including, by way of non-limiting example: the computerized system of training a machine learning system for managing a subject's nutrition, the computerized system for utilizing a machine learning system for managing a subject's nutrition, the processing and memory circuitry (PMC) of these systems as disclosed in the present application.

The operations in accordance with the teachings herein can be performed by a computer specially constructed for the desired purposes or by a general purpose computer specially configured for the desired purpose by a computer program stored in a non-transitory computer readable storage medium.

The term "non-transitory computer readable storage medium" used herein should be expansively construed to cover any volatile or non-volatile computer memory suitable to the presently disclosed subject matter.

Embodiments of the presently disclosed subject matter are not described with reference to any particular programming language. It will be appreciated that a variety of programming languages may be used to implement the teachings of the presently disclosed subject matter as described herein.

As used herein, the phrase "for example," "such as", "for instance", "e.g." and variants thereof describe non-limiting embodiments of the presently disclosed subject matter. Reference in the specification to "certain embodiment", "one embodiment" or variants thereof means that a particular feature, structure or characteristic described in connection with the embodiment(s) is included in at least one embodiment of the presently disclosed subject matter.

It is appreciated that, unless specifically stated otherwise, certain features of the presently disclosed subject matter (including the "Annex"), which are described in the context of separate embodiments, can also be provided in combination in a single embodiment. Conversely, various features of the presently disclosed subject matter (including the "Annex"), which are described in the context of a single embodiment, can also be provided separately or in any suitable sub-combination.

In embodiments of the presently disclosed subject matter one or more stages illustrated in the figures may be executed in a different order and/or one or more groups of stages may be executed simultaneously and vice versa.

It is to be understood that the invention is not limited in its application to the details set forth in the description contained herein or illustrated in the drawings. The invention is capable of other embodiments and of being practiced and carried out in various ways. Hence, it is to be understood that the phraseology and terminology employed herein are for the purpose of description and should not be regarded as limiting. As such, those skilled in the art will appreciate that the conception upon which this disclosure is based may readily be utilized as a basis for designing other structures, methods, and systems for carrying out the several purposes of the presently disclosed subject matter.

It will also be understood that the system according to the invention may be, at least partly, implemented on a suitably programmed computer. Likewise, the invention contemplates a computer program being readable by a computer for executing the method of the invention. The invention further contemplates a non-transitory computer readable medium (such as memory or storage) tangibly embodying a program of instructions executable by the computer for executing the method of the invention.

The non-transitory computer readable storage medium causing a processor to carry out aspects of the present invention can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing.

Those skilled in the art will readily appreciate that various modifications and changes can be applied to the embodiments of the invention as hereinbefore described without departing from its scope, defined in and by the appended claims.

The invention claimed is:

1. A computerized method for managing a subject's nutrition of a subject, the method comprising:

a) providing a subject-specific biologically-derived learning personalized metabolic model that is constrained based at least in part on a plurality of identified personalized metabolic parameters that are associated with the subject, wherein each personalized metabolic parameter has a respective range of values, wherein the plurality of identified personalized metabolic parameters comprises at least the insulin sensitivity and gastric emptying rate parameters;

b) obtaining output virtual data sets from the subject-specific biologically-derived learning personalized metabolic model, based on at least:

(i) input personalized data indicative of virtual metabolic parameter sets that fall within the respective range of values of each of the plurality of identified personalized metabolic parameters, and (ii) virtual meal scenarios that comprises simulated virtual consumed carbohydrate content, wherein the output virtual data sets comprise data indicative of a set of virtual biomarker levels for at least one biomarker, and wherein at least one virtual biomarker level of the set of virtual biomarker levels comprises glucose response;

c) transforming, by at least one processor, the output virtual data sets to produce data indicative of estimates of unknown variables for the subject, wherein the estimates of unknown variables comprise at least one of: carbohydrates intake during last time step (dC), carbohydrates amount in stomach compartment, carbohydrates amount in the gut compartment (Gq), plasma glucose concentration (G), or any combination thereof;

d) training a computational machine learning system, by utilizing a data training set that comprises at least in part the simulated meal scenarios and the estimates of unknown variables for the subject, to obtain a subject-specific computational machine learning model having a set of personalized machine learning parameter values that characterizes the subject, thereby allowing the subject-specific computational machine learning model to identify real retroactive carbohydrate content consumed by the subject, at least one real retroactive meal time, or both, based on the glucose response of the subject, wherein the subject-specific computational machine learning model is distinct from the subject-specific biologically-derived personalized metabolic model;

e) receiving, by the at least one processor, real-time biomarker data indicative of at least one biomarker level of the at least one biomarker in a bodily fluid of the subject during a real-time operation phase;

f) transforming, by the at least one processor, the real-time biomarker data to produce data indicative of real-time estimates of unknown variables for the subject that are selected from the group comprising at least one of: carbohydrates intake during a last time step (dC), carbohydrates amount in the gut compartment (Gq), plasma glucose concentration (G), or any combination thereof;

g) executing, by the at least one processor, the subject-specific computational machine learning model to determine the real retroactive carbohydrate content consumed by the subject, the at least one real retroactive meal time, or both, based on at least the real-time unknown variable data and the set of personalized machine learning parameter values that characterize the subject; and h) performing, by the at least one processor, at least one of:

(i) automatically adjusting the subject's subsequent food consumption according to the real retroactive carbohydrate content, the at least one real retroactive meal time, or both;

(ii) when the subject is a diabetes patient, automatically adjusting the subject's subsequent insulin administration according to the real retroactive carbohydrate content consumed by the subject, the at least one real retroactive meal time, or both;

(iii) when the subject is on a weight loss program, on a weight loss medication, or both, automatically adjusting the subject's subsequent medication dose according to the at least one nutritional intake pattern; or (iv) any combination thereof.

2. The method according to claim 1, wherein the data training set comprises at least one of (i) data indicative of the glucose response of the subject, (ii) data indicative of previous insulin administration, or a combination thereof.

3. The method according to claim 1, wherein the method further comprises receiving, by the at least one processor, data indicative of at least one of heart rate, temperature, heart rate variability, body movement, sleep time period, or any combination thereof.

4. The method according to claim 1, wherein the unknown variables are selected from the group that further comprises insulin administration during last time step (dI), active insulin (X), plasma insulin (I), and amount of non-monomeric and monomeric insulin in subcutaneous compartments (Isc1/Isc2).

5. The method according to claim 1, wherein the input personalized data is further indicative of a plurality of meal scenarios, a plurality of insulin administration scenarios, or both; and wherein the plurality of metabolic parameter sets.

6. The method of claim 1, the method further comprising detecting at least one of the at least one nutritional intake pattern, the ability to meet the at least one nutritional goal, the identification of the at least one problematic behavior, or any combination thereof;

evaluating the subject's success in reaching a diet goal; and generating at least one dietary suggestion for glycemic and weight control.

7. The method of claim 1, wherein said method further comprises: generating an estimation of at least one of glucose sensitivity, insulin resistance, continuous blood insulin level, risk of diabetes, risk of a heart disease, or any combination thereof.

8. The method of claim 1, wherein the subject is a diabetes patient.

9. The method according to claim 1, wherein the subject-specific biologically-derived learning personalized metabolic model is trained using calibration meal data that comprises a first number of real calibration meals and a second number of virtual meals, wherein the second number is larger than the first number.

10. A computerized system for managing a subject's nutrition of a subject, the computerized system comprising at least one processor and memory circuitry (PMC), storing instructions that, when executed by the at least one processor, cause the computerized system to:

provide a subject-specific biologically-derived learning personalized metabolic model that is constrained based at least in part on a plurality of identified personalized metabolic parameters that are associated with the subject, wherein each personalized metabolic parameter has a respective range of values, wherein the plurality of identified personalized metabolic parameters comprises at least the insulin sensitivity and gastric emptying rate parameters;

obtain output virtual data sets from the subject-specific biologically-derived learning personalized metabolic model, based on at least:

(i) input personalized data indicative of virtual metabolic parameter sets that fall within the respective range of values of each of the plurality of identified personalized metabolic parameters, and (ii) virtual meal scenarios that comprises simulated virtual consumed carbohydrate content, wherein the output virtual data sets comprise data indicative of a set of virtual biomarker levels for at least one biomarker, and wherein at least one virtual biomarker level of the set of virtual biomarker levels comprises glucose response;

transform the output virtual data sets to produce data indicative of estimates of unknown variables for the subject, wherein the estimates of unknown variables comprise at least one of: carbohydrates intake during last time step (dC), carbohydrates amount in stomach compartment, carbohydrates amount in the gut compartment (Gq), plasma glucose concentration (G), or any combination thereof;

train a computational machine learning system, by utilizing a data training set that comprises at least in part the simulated meal scenarios and the estimates of unknown variables for the subject, to obtain a subject-specific computational machine learning model having a set of personalized machine learning parameter values that characterizes the subject, thereby allowing the subject-specific computational machine learning model to identify real retroactive carbohydrate content consumed by the subject, at least one real retroactive meal time, or both, based on the glucose response of the subject, wherein the subject-specific computational machine learning model is distinct from the subject-specific biologically-derived personalized metabolic model;

receive real-time biomarker data indicative of at least one biomarker level of the at least one biomarker in a bodily fluid of the subject during a real-time operation phase;

transform the real-time biomarker data to produce data indicative of real-time estimates of unknown variables for the subject that are selected from the group comprising at least one of: carbohydrates intake during a last time step (dC), carbohydrates amount in the gut compartment (Gq), plasma glucose concentration (G), or any combination thereof;

execute the subject-specific computational machine learning model to determine the real retroactive carbohydrate content consumed by the subject, the at least one real retroactive meal time, or both, based on at least the real-time unknown variable data and the set of personalized machine learning parameter values that characterize the subject; and perform at least one of:

(i) automatically adjusting the subject's subsequent food consumption according to the real retroactive carbohydrate content, the at least one real retroactive meal time, or both;

(ii) when the subject is a diabetes patient, automatically adjusting the subject's subsequent insulin administration according to the real retroactive carbohydrate content consumed by the subject, the at least one real retroactive meal time, or both;

(iii) when the subject is on a weight loss program, on a weight loss medication, or both, automatically adjusting the subject's subsequent medication dose according to the at least one nutritional intake pattern; or (iv) any combination thereof.

11. The system according to claim 10, wherein the data training set comprises at least one of (i) data indicative of the glucose response of the subject, (ii) data indicative of previous insulin administration, or a combination thereof.

12. The system according to claim 10, wherein the instructions, when executed by the at least one processor, further cause the computerized system to receive data indicative of at least one of heart rate, temperature, heart rate variability, body movement, sleep time period, or any combination thereof.

13. The system according to claim 10, wherein the unknown variables are selected from the group that further comprises insulin administration during last time step (dI), active insulin (X), plasma insulin (I), and amount of non-monomeric and monomeric insulin in subcutaneous compartments (Isc1/Isc2).

14. The system according to claim 10, wherein the input personalized data is further indicative of a plurality of meal scenarios, a plurality of insulin administration scenarios, or both; and wherein the plurality of metabolic parameter sets are random parameter sets.

15. The system according to claim 10, wherein the instructions, when executed by the at least one processor, further cause the computerized system to generate an estimation of at least one of glucose sensitivity, insulin resistance, continuous blood insulin level, risk of diabetes, risk of a heart disease, or any combination thereof.

16. The system according to claim 10, wherein the subject-specific biologically-derived learning personalized metabolic model is trained using calibration meal data that comprises a first number of real calibration meals and a second number of virtual meals, wherein the second number is larger than the first number.

17. The system according to claim 10, wherein the computational machine learning system is of Convolutional Neural Networks (CNN) type.

18. The system according to claim 10, wherein the computational machine learning system is of Recurrent Neural Network (RNN) type.

19. A non-transitory computer readable medium comprising instructions that, when executed by a computer, cause the computer to perform method steps, comprising:

providing a subject-specific biologically-derived learning personalized metabolic model that is constrained based at least in part on a plurality of identified personalized metabolic parameters that are associated with the subject, wherein each personalized metabolic parameter has a respective range of values, wherein the plurality of identified personalized metabolic parameters comprises at least the insulin sensitivity and gastric emptying rate parameters;

obtaining output virtual data sets from the subject-specific biologically-derived learning personalized metabolic model, based on at least:

(i) input personalized data indicative of virtual metabolic parameter sets that fall within the respective range of values of each of the plurality of identified personalized metabolic parameters, and (ii) virtual meal scenarios that comprises simulated virtual consumed carbohydrate content, wherein the output virtual data sets comprise data indicative of a set of virtual biomarker levels for at least one biomarker, and wherein at least one virtual biomarker level of the set of virtual biomarker levels comprises glucose response;

transforming the output virtual data sets to produce data indicative of estimates of unknown variables for the subject, wherein the estimates of unknown variables comprise at least one of: carbohydrates intake during last time step (dC), carbohydrates amount in stomach compartment, carbohydrates amount in the gut compartment (Gq), plasma glucose concentration (G), or any combination thereof;

training a computational machine learning system, by utilizing a data training set that comprises at least in part the simulated meal scenarios and the estimates of unknown variables for the subject, to obtain a subject-specific computational machine learning model having a set of personalized machine learning parameter values that characterizes the subject, thereby allowing the subject-specific computational machine learning model to identify real retroactive carbohydrate content consumed by the subject, at least one real retroactive meal time, or both, based on the glucose response of the subject, wherein the subject-specific computational machine learning model is distinct from the subject-specific biologically-derived personalized metabolic model;

receiving real-time biomarker data indicative of at least one biomarker level of the at least one biomarker in a bodily fluid of the subject during a real-time operation phase;

transforming the real-time biomarker data to produce data indicative of real-time estimates of unknown variables for the subject that are selected from the group comprising at least one of: carbohydrates intake during a last time step (dC), carbohydrates amount in the gut compartment (Gq), plasma glucose concentration (G), or any combination thereof;

executing the subject-specific computational machine learning model to determine the real retroactive carbohydrate content consumed by the subject, the at least one real retroactive meal time, or both, based on at least the real-time unknown variable data and the set of personalized machine learning parameter values that characterize the subject; and performing at least one of:

(i) automatically adjusting the subject's subsequent food consumption according to the real retroactive carbohydrate content, the at least one real retroactive meal time, or both;

(ii) when the subject is a diabetes patient, automatically adjusting the subject's subsequent insulin administration according to the real retroactive carbohydrate content consumed by the subject, the at least one real retroactive meal time, or both;

(iii) when the subject is on a weight loss program, on a weight loss medication, or both, automatically adjusting the subject's subsequent medication dose according to the at least one nutritional intake pattern; or (iv) any combination thereof.

20. The non-transitory computer readable medium according to claim 19, further wherein the instructions, when executed by the computer, cause the computer to perform method steps, comprising:

generating an estimation of at least one of glucose sensitivity, insulin resistance, continuous blood insulin level, risk of diabetes, risk of a heart disease, or any combination thereof.

* * * * *